(12) United States Patent
Liss et al.

(10) Patent No.: US 9,115,390 B2
(45) Date of Patent: Aug. 25, 2015

(54) METHOD FOR DETERMINING FRAMESHIFT MUTATIONS IN CODING NUCLEIC ACIDS

(75) Inventors: Michael Liss, Regenburg (DE); Jutta Derer, Regensburg (DE); Frank Notka, Regensburg (DE); Daniela Daubert, Landshut (DE); Claudia Benkel, Regensburg (DE)

(73) Assignee: GeneArt AG, Regensburg (DE)

( * ) Notice: Subject to any disclaimer, the term of this patent is extended or adjusted under 35 U.S.C. 154(b) by 600 days.

(21) Appl. No.: 12/714,835

(22) Filed: Mar. 1, 2010

(65) Prior Publication Data

US 2010/0297642 A1 Nov. 25, 2010

Related U.S. Application Data

(63) Continuation-in-part of application No. PCT/EP2008/009223, filed on Oct. 31, 2008.

(30) Foreign Application Priority Data

Nov. 2, 2007 (DE) .......... 10 2007 052 344
Mar. 2, 2009 (DE) .......... 10 2009 011 253

(51) Int. Cl.
*C12Q 1/68* (2006.01)
*C12Q 1/02* (2006.01)
*C12N 15/63* (2006.01)
*C12N 15/67* (2006.01)

(52) U.S. Cl.
CPC .............. *C12Q 1/6827* (2013.01); *C12N 15/63* (2013.01); *C12N 15/67* (2013.01); *C12Q 1/6897* (2013.01)

(58) Field of Classification Search
None
See application file for complete search history.

(56) References Cited

U.S. PATENT DOCUMENTS

| 5,876,940 | A | 3/1999 | Groden et al. |
| 6,391,641 | B1 | 5/2002 | Julin et al. |
| 6,682,885 | B1 * | 1/2004 | Kanamaru et al. ........... 435/6.11 |
| 2004/0234987 | A1 | 11/2004 | Brem et al. |

FOREIGN PATENT DOCUMENTS

| DE | 10107317 | A1 | 9/2002 |
| DE | 102007052344 | B3 | 3/2009 |
| EP | 0872560 | A1 | 10/1998 |
| EP | 1275736 | A1 | 1/2003 |
| JP | 2004242583 | A | 9/2004 |
| WO | 0206527 | A2 | 1/2002 |
| WO | 2008051619 | A2 | 5/2008 |
| WO | 2008077881 | A1 | 7/2008 |

OTHER PUBLICATIONS

Gerth et al. A second-generation system for unbiased reading frame selection. Protein Engineering, Design & Selection, vol. 17, No. 7, pp. 595-602, Aug. 2004.*
Faix et al. Phage display of cDNA libraries: enrichment of cDNA expression using open reading frame selection. BioTechniques, vol. 36, pp. 1018-1029, Jun. 2004.*
XL1-Blue MRF' Supercompetent Cells (Catalog #200230, printed http://www.chem-agilent.com/pdf/strata/200230.pdf on Feb. 7, 2012 as pp. 1/2 to 2/2.*
van de Guchte et al. Distance-dependent translational coupling and interference in *Lactococcus lactis*. Molecular and General Genetics, vol. 227, pp. 65-71, 1991.*
Ropp et al. Aequorea green fluorescent protein analysis by flow cytometry. Cytometry, vol. 21, pp. 309-317, 1995.*
Finch et al. Complete nucleotide sequence of recD, the structural gene of the alpha subunit of Exonuclease V of *Escherichia coli*. Nucleic Acids Research, vol. 14, No. 21, pp. 8583-8594, 1986.*
European Patent Office. "Search Report." EP10155226. Applicant: Geneart Ag. Date: Jun. 24, 2010.
European Patent Office. "English Abstract, Patent Abstracts of Japan." JP 2004242583, Applicant: National Institute of Advanced Industrial & Tech, Sep. 2, 2004.
Cabantous, Stephane et al. "New Molecular Reporters for Rapid Protein Folding Assays." (PLoS One), Jun. 11, 2008, 1-10, 3:6.
Nagase, Takahiro et al. "Exploration of Human ORFeome: High-Throughput Preparation of ORF Clones and Efficient Characterization of Their Protein Products." (DNA Research), Mar. 2, 2008, 137-149, vol. 15.
Okada, Numata K et al. "Comparative analysis of cis-encoded antisense RNAs in eukaryotes." (Gene), Dec. 13, 2006, 134-41, vol. 392.
Ohashi-Kunihiro et al. "A novel vector for positive selection of inserts harboring an open reading frame by translational coupling." (Benchmarks), Dec. 2007, 751-754, 43:6. BioTechniques.
Espacenet Database: "English Abstract—Methods for Detecting Mutations." DE10107317A1, Applicant: Max-Planck-Gesellschaft, Sep. 9. 2012.
World Intellectual Property Organization: "English Abstract (57)" of WO2009/056343 (also published version of DE102007052344), Applicant: Geneart, Ag. May 7, 2009.

* cited by examiner

*Primary Examiner* — Jennifer Dunston

(57) ABSTRACT

The present invention relates to a method for identifying frameshift mutations in coding nucleic acid sequences.

10 Claims, 11 Drawing Sheets

Figure 1:
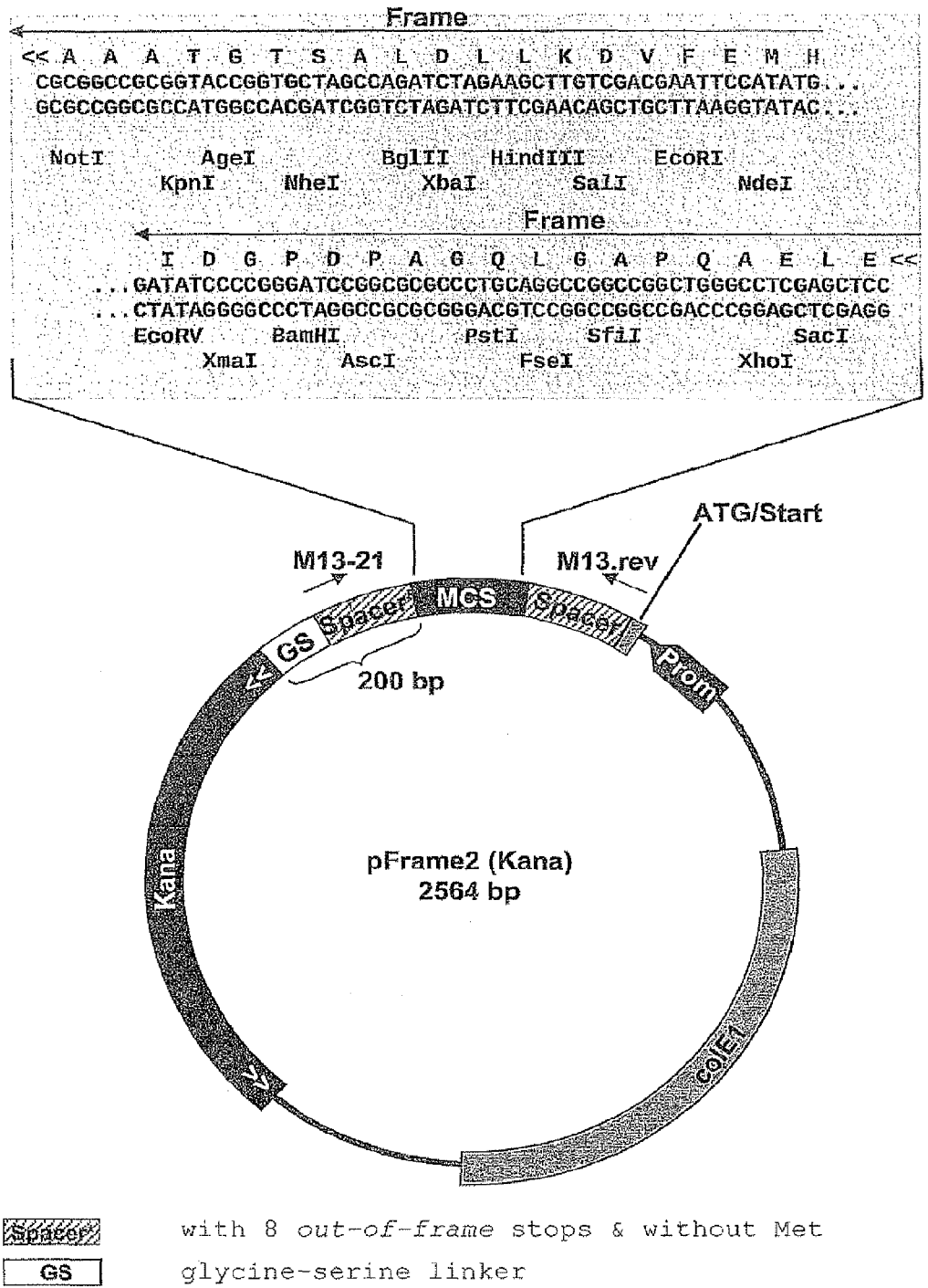

Figure 3
A) eGFP(-) sequence map (reverse complement)
Top: translation of minus strand
Bottom: translation of plus strand (wt protein)

```
        E  L  K  L  V  Q  F  I  H  A  Q  G  N  T  S  G  G  H  E  F  Q  Q  H  H  V  I  T
  1   GAGCTCAAGCTTGTACAGTTCATCCATGCCCAGGGTAATACCAGCGGCGGTCACGAATTCCAGCAGCACCATGTGATCAC   80
  1   CTCGAGTTCGAACATGTCAAGTAGGTACGGGTCCCATTATGGTCGCCGCCAGTGCTTAAGGTCGTCGTGGTACACTAGTG   80
        L  E  L  K  Y  L  E  D  M  G  L  T  I  G  A  A  T  V  F  E  L  L  V  M  H  D  R

F  F  V  R  I  F  A  Q  G  A  L  G  A  Q  V  V  V  I  R  Q  Q  H  R  A  I  T
 81   GTTTTTCGTTCGGATCTTTGCTCAGGGCGCTCTGGGTGCTCAGGTAGTGGTTATCCGGCAGCAGCACCGGGCCATCACCA  160
 81   CAAAAAGCAAGCCTAGAAACGAGTCCCGCGAGACCCACGAGTCCATCACCAATAGGCCGTCGTCGTGGCCCGGTAGTGGT  160
        K  E  N  P  D  K  S  L  A  S  Q  T  S  L  Y  H  N  D  P  L  L  V  P  G  D  G

N  R  G  V  L  L  V  V  I  G  Q  L  H  A  A  I  F  D  V  V  A  D  F  E  V  H  F
161   ATCGGGGTGTTCTGCTGGTAGTGATCGGCCAGCTGCACGCTGCCATCTTCGATGTTGTGGCGGATTTTGAAGTTCACTTT  240
161   TAGCCCCACAAGACGACCATCACTAGCCGGTCGACGTGCGACGGTAGAAGCTACAACACCGCCTAAAACTTCAAGTGAAA  240
        I  P  T  N  Q  Q  Y  H  D  A  L  Q  V  S  G  D  E  I  N  H  R  I  K  F  N  V  K

D  A  V  F  L  F  I  G  H  D  V  H  V  V  A  V  V  V  V  F  Q  F  V  A  Q  D  V
241   GATGCCGTTTTTCTGTTTATCGGCCATGATGTACACGTTGTGGCTGTTGTAGTTGTATTCCAGTTTGTGGCCCAGGATGT  320
241   CTACGGCAAAAAGACAAATAGCCGGTACTACATGTGCAACACCGACAACATCAACATAAGGTCAAACACCGGGTCCTACA  320
        I  G  N  K  Q  K  D  A  M  I  Y  V  N  H  S  N  Y  N  Y  E  L  K  H  G  L  I  N

T  V  L  F  K  V  D  A  F  Q  F  D  T  V  H  Q  G  I  A  F  E  F  H  F  G  T
321   TACCGTCGTCTTTAAAGTCGATGCCTTTCAGTTCGATACGGTTCACCAGGGTATCGCCTTCGAATTTCACTTCGGCACGG  400
321   ATGGCAGCAGAAATTTCAGCTACGGAAAGTCAAGCTATGCCAAGTGGTCCCATAGCGGAAGCTTAAAGTGAAGCCGTGCC  400
        G  D  E  K  F  D  I  G  K  L  E  I  R  N  V  L  T  D  G  E  F  K  V  E  A  R

G  F  V  V  A  I  I  F  E  E  N  G  T  F  L  H  V  A  F  R  H  G  A  F  E  E  I
401   GTTTTGTAGTTGCCATCATCTTTGAAGAAAATGGTACGTTCCTGCACGTAGCCTTCCGGCATGGCGCTTTTGAAGAAATC  480
401   CAAAACATCAACGGTAGTAGAAACTTCTTTTACCATGCAAGGACGTGCATCGGAAGGCCGTACCGCGAAAACTTCTTTAG  480
        T  K  Y  N  G  D  D  K  F  F  I  T  R  E  Q  V  Y  G  E  P  M  A  S  K  F  F  D

V  L  F  H  V  I  R  V  A  R  E  A  L  H  A  V  G  Q  G  G  H  Q  G  R  P  R  H
481   GTGCTGTTTCATGTGATCCGGGTAGCGAGAGAAGCACTGCACGCCGTAGGTCAGGGTGGTCACCAGGGTCGGCCACGGCA  560
481   CACGACAAAGTACACTAGGCCCATCGCTCTCTTCGTGACGTGCGGCATCCAGTCCCACCAGTGGTCCCAGCCGGTGCCGT  560
        H  Q  K  M  H  D  P  Y  R  S  F  C  Q  V  G  Y  T  L  T  T  V  L  T  P  W  P  V

R  Q  F  A  G  G  T  D  E  F  Q  G  Q  F  A  V  G  G  I  T  F  T  F  A  G  H
561   CCGGCAGTTTGCCGGTGGTACAGATGAATTTCAGGGTCAGTTTGCCGTAGGTGGCATCACCTTCACCTTCGCCGGACACG  640
561   GGCCGTCAAACGGCCACCATGTCTACTTAAAGTCCCAGTCAAACGGCATCCACCGTAGTGGAAGTGGAAGCGGCCTGTGC  640
        P  L  K  G  T  T  C  I  F  K  L  T  L  K  G  Y  T  A  D  G  E  G  E  G  S  V

A  E  F  V  A  V  H  I  A  I  Q  F  H  Q  N  R  H  H  A  G  E  Q  F  F  A  F  G
641   CTGAATTTGTGGCCGTTCACATCGCCATCCAGTTCCACCAGAATCGGCACCACGCCGGTGAACAGTTCTTCGCCTTTGGA  720
641   GACTTAAACACCGGCAAGTGTAGCGGTAGGTCAAGGTGGTCTTAGCCGTGGTGCGGCCACTTGTCAAGAAGCGGAAACCT  720
        S  F  K  H  G  N  V  D  G  D  L  E  V  L  I  P  V  V  G  T  F  L  E  E  G  K  S

H  H  M  G  T
721   CACCATATGGGTACC                                                                   735
721   GTGGTATACCCATGG                                                                   735
        V  M  H  T  G
```

Figure 3(continued)

B) Neuraminidase (-) sequence map (reverse complement)
Top: translation of minus strand
Bottom: translation of plus strand (wt protein)

```
          E  L  S  R  G  S  S  S  L  V  D  G  E  G  Q  L  G  A  V  G  P  G  P  A  H  G  V
  1   GAGCTCTCTAGAGGATCCTCATCACTTGTCGATGGTGAAGGGCAGCTCGGCGCCGTCGGGCCAGGACCAGCTCACGGTGT    80
  1   CTCGAGAGATCTCCTAGGAGTAGTGAACAGCTACCACTTCCCGTCGAGCCGCGGCAGCCCGGTCCTGGTCGAGTGCCACA    80
          L  E  R  S  S  G  [ ]  K  D  I  T  F  P  L  E  A  G  D  P  W  S  W  S  V  T  D

A  V  H  A  A  K  A  D  A  A  A  A  G  P  D  G  A  L  F  G  P  A  S  D  Q  L
 81   CCCTGTTCACGCCGCAAAAGCTGATGCTGCTGCCGCTGGTCCAGATGGTGCTCTCTTTGGGCCTGCCTCTGATCAGCTCC   160
 81   GGGACAAGTGCGGCGTTTTCGACTACGACGACGGCGACCAGGTCTACCACGAGAGAAACCCGGACGGAGACTAGTCGAGG   160
          S  N  V  G  C  F  S  I  S  S  G  G  T  W  I  T  S  E  K  P  R  G  R  I  L  E

H  P  K  A  G  P  D  A  V  Q  A  G  Q  L  G  V  L  H  E  A  A  G  V  A  G  P  V
161   ACCCAAAAGCAGGGCCGGATGCAGTCCAGGCCGGTCAGCTCGGGGTGCTGCACGAAGCTGCCGGAGTAGCCGGACCAGTC   240
161   TGGGTTTTCGTCCCGGCCTACGTCAGGTCCGGCCAGTCGAGCCCCACGACGTGCTTCGACGGCCTCATCGGCCTGGTCAG   240
          V  W  F  C  P  R  I  C  D  L  G  T  L  E  P  H  Q  V  F  S  G  S  Y  G  S  W  D

G  D  G  H  D  V  L  L  H  A  E  A  A  V  G  P  G  P  A  V  G  V  P  D  H  L  E
241   GGTGATGGCCACGATGTCCTGCTTCACGCTGAAGCTGCTGTCGGTCCCGGTCCAGCCGTTGGGGTCCCAGATCATCTCGA   320
241   CCACTACCGGTGCTACAGGACGAAGTGCGACTTCGACGACAGCCAGGGCCAGGTCGGCAACCCCAGGGTCTAGTAGAGCT   320
          T  I  A  V  I  D  Q  K  V  S  F  S  S  D  T  G  T  W  G  N  P  D  W  I  M  E  F

A  G  S  A  V  G  A  L  G  P  A  D  P  H  A  V  A  V  L  E  A  E  A  L  H  A
321   AGCCGGATCTGCTGTTGGTGCTCTTGGTCCGGCCGATCCACACGCCGTCGCCGTACTTGAAGCTGAAGCCCTTCACGCCG   400
321   TCGGCCTAGACGACAACCACGAGAACCAGGCCGGCTAGGTGTGCGGCAGCGGCATGAACTTCGACTTCGGGAAGTGCGGC   400
          G  S  R  S  N  T  S  K  T  R  G  I  W  V  G  D  G  Y  K  F  S  F  G  K  V  G

V  G  A  I  G  A  H  C  S  A  A  A  C  A  I  V  G  P  G  V  V  A  E  H  S  A  A
401   TAGGCGCCATTGGGGCTCATGGGTCCGCAGCTGCCTGTGCCATCGTTGGGCCTGGGGTTGTCGCCGAACACTCCGCTGCA   480
401   ATCCGCGGTAACCCCGAGTACCCAGGCGTCGACGGACACGGTAGCAACCCGGACCCCAACAGCGGCTTGTGAGGCGACGT   480
          Y  A  G  N  P  S  M  P  G  C  S  G  T  G  D  N  P  R  P  N  D  G  F  V  G  S  C

D  V  A  D  L  V  F  Q  V  L  V  E  G  H  P  G  P  V  A  A  V  P  V  V  P  A  H
481   GATGTAGCCGATCTGGTATTCCAGGTTCTGGTTGAAGGACACCCAGGGCCGGTTGCTCCGTGCCAGTTGTCCCGGCACA    560
481   CTACATCGGCTAGACCATAAGGTCCAAGACCAACTTCCTGTGGGTCCCGGCCAACGACGGCACGGTCAACAGGGCCGTGT   560
          I  Y  G  I  Q  Y  E  L  N  Q  N  F  S  V  W  P  R  N  S  G  H  W  N  D  R  C  V

A  G  D  L  A  G  V  G  V  A  A  A  F  L  V  V  V  V  G  G  V  Q  L  H  A  L
561   CGCAGGTGATCTCGCCGGCGTCGGGGTAGCAGCTGCATTCCTCGTAGTGGTAGTTGGGGGCGTCCAGCTCCACGCTCTTC   640
561   GCGTCCACTAGAGCGGCCGCAGCCCCATCGTCGACGTAAGGAGCATCACCATCAACCCCGCAGGTCGAGGTGCGAGAAG   640
          C  T  I  E  G  A  D  P  Y  C  S  C  E  E  Y  H  Y  N  P  A  D  L  E  V  S  K

H  H  L  A  L  F  H  L  E  N  L  V  G  G  L  P  V  A  G  A  V  G  H  H  G  E  A
641   ACCACCTTGCCCTTTTGCCATCTTGAAAATCTTGTAGGAGGCCTGCCGTTGCTGGGGCCGTCGGTCATCACGGTGAAGCA   720
641   TGGTGGAACGGGAAAAGGTAGAACTTTTAGAACATCCTCCGGACGGGCAACGACCCCGGCAGCCAGTAGTGCCACTTCGT   720
          V  V  K  G  K  E  M  K  F  I  K  Y  S  A  Q  G  N  S  P  G  D  T  M  V  T  F  C

A  A  V  H  A  G  A  L  A  F  L  G  P  Q  D  V  V  P  P  A  L  D  G  V  G  D  D
721   GCTGCCGTTCACGCAGGCGCACTCGCTTTCCTGGGTCCGCAGGATGTTGTTCCGCCAGCTCTTGATGGTGTCGGTGATGA   800
721   CGACGGCAAGTGCGTCCGCGTGAGCGAAAGGACCCAGGCGTCCTACAACAAGGCGGTCGAGAACTACCACAGCCACTACT   800
          S  G  N  V  C  A  C  E  S  E  Q  T  R  L  I  N  N  R  W  S  K  I  T  D  T  I  I

A  V  V  L  Q  H  S  D  S  A  V  V  R  A  A  D  A  D  G  Q  P  A  G  A  V  V
801   TGCCGTTGTACTTCAGCACAGCGACAGCGCCGTTGTCAGGGCCGCTGATGCCGATGGTCAGCCAGCTGGTGCCGTCGTGG   880
801   ACGGCAACATGAAGTCGTGTCGCTGTCGCGGCAACAGTCCCGGCGACTACGGCTACCAGTCGGTCGACCACGGCAGCACC   880
          G  N  Y  K  L  V  A  V  A  G  N  D  P  G  S  I  G  I  T  L  W  S  T  G  D  H
```

Figure 3 (continued)

```
          A  G  A  G  G  P  G  H  A  L  E  P  A  V  V  G  A  G  S  L  A  H  G  A  A  H  Q
881   CAGGCGCTGGCGGACCAGGCCACGCTCTCGAACCGGCTGTTTGTAGGGGCTGGGAGCCTCGCCCACGGGGCAGCTCATCAG   960
881   GTCCGCGACCGCCTGGTCCGGTGCCAGAGCTTGGCCGACAACATCCCCGACCCTCGGAGCGGGTGCCCCGTCGAGTAGTC   960
          C  A  S  A  S  W  A  V  S  E  F  R  S  N  Y  P  S  P  A  E  G  V  P  C  S  M  L

G  P  V  G  A  S  V  L  H  G  A  I  A  V  L  V  V  Q  Q  C  S  L  G  Q  E  E  G
961   GGTCCGGTGGGGGCTTCTGTCCTTCACGGTGCCATTGCTGTGCTTGTCGTTCAGCAGTGCTCCCTGGGTCAGGAAGAAGG   1040
961   CCAGGCCACCCCCGAAGACAGGAAGTGCCACGGTAACGACACGAACAGTCGTCACGAGGGACCCAGTCCTTCTTCC      1040
          T  R  H  P  S  R  D  K  V  T  G  N  S  H  K  D  N  L  L  A  G  Q  T  L  F  F  T

P  A  F  Q  V  A  A  A  D  E  G  L  P  D  H  E  H  V  A  L  A  A  D  P  D  V
1041  TCCGGCATTCCAGGTGGCTGCAGCTGATGAAGGGCTCCCGGATCACGAACACGTCGCCCTTGCTGCCGATCCGGATGTTG   1120
1041  AGGCCGTAAGGTCCACCGACGTCGACTACTTCCCGAGGGCCTAGTGCTTGTGCAGCGGGAACGACGGCTAGGCCTACAAC   1120
          R  C  E  L  H  S  C  S  T  F  P  E  R  I  V  F  V  D  G  K  S  G  I  R  I  N

V  V  L  A  V  H  G  P  A  P  D  G  A  Q  A  A  V  A  G  Q  G  H  A  S  H  G  L
1121  TTGTCCTTGCTGTGCACGGCCCAGCCCCGGATGGGGCACAGGCTGCTGTTGCCGCCAGGGTCACGCTAGCCACGGCCTT   1200
1121  AACAGGAACGACACGTGCCGGGTCGGGGCCTACCCCGTGTCCGACGACAACGGCCGGTCCCAGTGCGATCGGTGCCGGAA   1200
          N  D  K  S  H  V  A  W  G  R  I  P  C  L  S  S  N  G  A  L  T  V  S  A  V  A  K

L  G  Q  G  V  G  V  A  D  A  L  G  L  V  L  A  A  S  L  D  A  V  G  H  P  D  A
1201  CTCGGTCAGGGGGTTGGTGTTGCTGATGCTCTCGGCCTGGTGCTGGCTGCCGGTCTGGATGCTGTGGGACACCCAGATGC   1280
1201  GAGCCAGTCCCCCAACCACAACGACTACGAGAGCCGGACCACGACCGACGGCAGACCTACGACACCCTGTGGGTCTACG   1280
          E  T  L  P  N  T  N  S  I  S  E  A  Q  H  Q  S  G  T  Q  I  S  H  S  V  W  I  S

D  H  V  A  D  L  Q  H  Q  A  H  G  A  D  H  H  A  D  A  A  D  G  D  D  L  L
1281  TGATCATGTTGCCGATCTGCAGCATCAGGCTCACGGTGCCGATCACCATGCAGATGCTGCCGATGGTGATGATCTTCTGG   1360
1281  ACTAGTACAACGGCTAGACGTCGTAGTCCGAGTGCCACGGCTAGTGGTACGTCTACGACGGCTACCACTACTAGAAGACC   1360
          I  M  N  G  I  Q  L  M  L  S  V  T  G  I  V  M  C  I  S  G  I  T  I  I  K  Q

V  G  V  H  G  G  A  A  A  I  S  G  T
1361  TTGGGGTTCATGGTGGCGCGGCCGCGATATCGGGTACC   1398
1361  AACCCCAAGTACCACCGCGCCGGCGCTATAGCCCATGG   1398
          N  P  N  M  T  A  R  G  R  Y  R  T  G
```

C) MBD4(-) sequence map (reverse complement)
Top: translation of minus strand
Bottom: translation of plus strand (wt protein)

```
          E  L  E  S  S  A  Q  G  Q  L  L  V  V  L  P  Q  P  V  V  V  L  V  Q  L  V  V  L
1     GAGCTCGAGTCATCAGCTCAGGGACAGCTTCTCGTGGTTCTCCCACAGCCAGTCGTGGTACTTGTTCAGCTTGTGGTCCT   80
1     CTCGAGCTCAGTAGTCGAGTCCCTGTCGAAGAGCACCAAGAGGGTGTCGGTCAGCACCATGAACAAGTCGAACACCAGGA   80
          L  E  L  ░░  S  L  S  L  K  E  H  N  E  W  L  W  D  H  Y  K  N  L  K  H  D  E

G  V  H  L  L  P  L  V  H  A  E  D  P  V  A  V  V  A  V  L  A  D  A  V  Q  L
81    CGGGGTGCACCTGCTTCCACTCGTTCACGCAGAAGATCCGGTAGCTGTCGTTGCCGTACTTGCCGATGCCGTGCAGCTCG   160
81    GCCCCACGTGGACGAAGGTGAGCAAGTGCGTCTTCTAGGCCATCGACAGCAACGGCATGAACGGCTACGGCACGTCGAGC   160
          P  H  V  Q  K  W  E  N  V  C  F  I  R  Y  S  D  N  G  Y  K  G  I  G  H  L  E

D  G  V  L  P  L  L  G  Q  V  L  V  A  E  L  H  D  G  L  G  P  Q  V  V  Q  A  Q
161   ATGGGGTACTTCCACTGCTTGGTCAGGTACTCGTCGCTGAACTTCACGATGGTCTTGGCCCTCAGGTCGTACAGGCCCAG   240
161   TACCCCATGAAGGTGACGAACCAGTCCATGAGCAGCGACTTGAAGTGCTACCAGAACCGGGAGTCCAGCATGTCCGGGTC   240
          I  P  Y  K  W  Q  K  T  L  Y  E  D  S  F  K  V  I  T  K  A  R  L  D  Y  L  G  L

G  L  Q  Q  L  A  H  V  P  P  V  G  G  P  G  H  L  G  A  G  V  L  F  Q  E  L  P
241   GGGCTTCAGCAGCTCGCTCACGTCCCGCCAGTCGGCGGTCCTGGCCACCTCGGCGCTGGGGTACTTTTCCAGGAACTTCC   320
241   CCCGAAGTCGTCGAGCGAGTGCAGGGCGGTCAGCCGCCAGGACCGGTGGAGCCGCGACCCCATGAAAAGGTCCTTGAAGG   320
          P  K  L  L  E  S  V  D  R  W  D  A  T  R  A  V  E  A  S  P  Y  K  E  L  F  K  W
```

Figure 3(continued)

```
                Q  H  G  D  G  H  L  A  A  G  P  V  Q  K  D  G  G  D  Q  Q  L  P  G  V  V  E
321  ACAGCACGGGGATGGCCATCTTGCCGCTGGTCCGGTTCAGAAAGATGGTGGCGATCAGCAGCTTCCAGGGGTCGTGGAAC  400
321  TGTCGTGCCCCTACCGGTAGAACGGCGACCAGGCCAAGTCTTTCTACCACCGCTAGTCGTCGAAGGTCCCCAGCACCTTG  400
              L  V  P  I  A  M  K  G  S  T  R  N  L  F  I  T  A  I  L  L  K  W  P  D  H  F

Q  G  F  L  D  Q  V  E  G  A  S  G  G  G  P  L  L  E  G  L  P  P  S  G  A  Q  G
401  AGGGTTTCCTGGACCAGGTTGAAGGGGCTTCTGGGGGGGGTCCACTTCTTGAAGGCCTTCCGCCTGGGGGGGCTCAGGGC  480
401  TCCCAAAGGACCTGGTCCAACTTCCCCGAAGACCCCCCCCAGGTGAAGAACTTCCGGAAGGCGGACCCCCCCGAGTCCCG  480
              L  T  E  Q  V  L  N  F  P  S  R  P  P  T  W  K  K  F  A  K  R  R  P  P  S  L  A

L  F  V  V  L  A  A  E  V  Q  A  G  L  S  P  L  D  L  G  P  G  D  G  V  L  G  E
481  CTCTTTGTTGTACTTGCTGCTGAAGTACAGGCTGGTCTTTCTCCGCTCGATCTGGGTCCGGGGGATGGTGTCCTCGGTGA  560
481  GAGAAACAACATGAACGACGACTTCATGTCCGACCAGAAAGAGGCGAGCTAGACCCAGGCCCCTACCACAGGAGCCACT  560
              E  K  N  Y  K  S  S  F  Y  L  S  T  K  R  R  E  I  Q  T  R  P  I  T  D  E  T  F

V  L  P  G  G  A  A  V  V  V  H  L  A  A  P  L  Q  D  V  G  V  Q  V  L  F  P
561  AGTCCTTCCGGGTGGGGCTGCAGTTGTTGTCCATCTCGCTGCCCCTCTTCAGGATGTCGGTGTGCAGGTGCTCTTTCCGC  640
561  TCAGGAAGGCCCACCCCGACGTCAACAACAGGTAGAGCGACGGGAGAAGTCCTACAGCCACACGTCCACGAGAAAGGCG  640
              D  K  R  T  P  S  C  N  N  D  M  E  S  G  R  K  L  I  D  T  H  L  H  E  K  R

L  H  H  L  H  L  G  A  D  F  L  A  F  Q  E  G  V  L  V  L  L  V  V  L  A  V  L
641  TCCACCACCTCCACCTTGGTGCCGATTTCCTCGCTTTCCAGGAAGGTGTCCTCGTACTTCTCGTTGTGCTCGCTGTCCTT  720
641  AGGTGGTGGAGGTGGAACCACGGCTAAAGGAGCGAAAGGTCCTTCCACAGGAGCATGAAGAGCAACACGAGCGACAGGAA  720
              E  V  V  E  V  K  T  G  I  E  E  S  E  L  F  T  D  E  Y  K  E  N  H  E  S  D  K

G  A  A  E  L  V  D  D  A  A  G  F  L  L  A  A  E  V  A  A  A  A  Q  A  P  L  F
721  GGCGCTGCAGAACTTGTTGATGATGCCGCTGGTTTTCTGCTCGCTGCAGAAGTTGCTGCCGCTGCTCAGGCTCCGCTCTT  800
721  CCGCGACGTCTTGAACAACTACTACGGCGACCAAAAGACGAGCGACGTCTTCAACGACGGCGACGAGTCCGAGGCGAGAA  800
              A  S  C  F  K  N  I  I  G  S  T  K  Q  E  S  C  F  N  S  G  S  S  L  S  R  E  K

L  L  H  Q  A  V  F  L  A  G  H  A  Q  C  L  A  A  G  S  G  V  A  D  A  H  G
801  TCTTCTTCACCCAGGCTGTTTTCCTCGCTGGTCACGCTCAGTGTCTCGCCGCAGGCTCCGGCGTCGCTGATGCACACGGTC  880
801  AGAAGAAGTGGTCCGACAAAGGAGCGACCAGTCGAGTCACAGAGCGGCGTCCGAGGCCGCAGCGACTACGTGTGCCAG  880
              K  K  V  L  S  N  E  E  S  T  V  S  L  T  E  G  C  A  G  A  D  S  I  C  V  T

P  V  Q  L  A  L  L  G  H  G  L  A  L  G  V  G  L  V  A  H  G  L  P  L  A  V  A
881  CGGTCCAGCTGGCTCTTCTGGGCCACGGGCTCGCTCTCGGCGTCGGCCTTGTTGCACACGGACTCCCGCTTGCTGTCGCT  960
881  GCCAGGTCGACCGAGAAGACCCGGTGCCCGAGCGAGAGCCGCAGCCGGAACAACGTGTGCCTGAGGGCGAACGACAGCGA  960
              R  D  L  Q  S  K  Q  A  V  P  E  S  E  A  D  A  K  N  G  V  S  F  R  K  S  D  S

L  H  E  A  A  A  A  L  P  A  A  L  L  G  F  L  D  G  D  A  L  Q  D  G  H  L  A
961  CTGCACGAAGCCGCTGCAGCTCTTCCTGCAGCCCTTCTTGGTTTTCTTGATGGGGATGCCCTTCAGGATGGTCACCTTGC  1040
961  GACGTGCTTCGGCGACGTCGAGAAGGACGTCGGGAAGAACCAAAAGAACTACCCCTACGGGAAGTCCTACCAGTGGAACG  1040
              Q  V  F  G  S  C  S  K  R  C  G  K  K  T  K  K  I  P  I  G  K  L  I  T  V  K  G

L  G  L  P  H  F  P  E  V  H  V  V  D  A  L  I  L  F  Q  Q  Q  V  G  A  G  E
1041 CCTTGGGCTTCCGCACTTTCCGGAAGTTCACGTCGTCGACGCCCTCATCCTCTTTCAGCAGCAGGTGGGTGCTGGTGAAG  1120
1041 GGAACCCGAAGGCGTGAAAGGCCTTCAAGTGCAGCAGCTGCGGGAGTAGGAGAAAGTCGTCGTCCACCCACGACCACTTC  1120
              K  P  K  R  V  K  R  F  N  V  D  D  V  G  E  D  E  K  L  L  L  H  T  S  T  F

V  A  Q  A  P  A  F  L  Q  F  G  A  R  A  G  G  H  E  H  V  F  L  A  L  G  P  G
1121 TTGCTCAGGCCCCTGCTTTCCTGCAGTTCGGAGCTAGAGCTGGGGGGCATGAACACGTCTTTCTTGCACTTCGACCGGGT  1200
1121 AACGAGTCCGGGGACGAAAGGACGTCAAGCCTCGATCTCGACCCCCGTACTTGTGCAGAAAGAACGTGAACCTGGCCCA  1200
              N  S  L  G  R  S  E  Q  L  E  S  S  S  S  P  P  M  F  V  D  K  K  C  K  S  R  T

P  Q  V  P  V  A  V  V  A  L  V  L  Q  V  A  G  Q  G  G  H  A  A  V  L  V  P  A
1201 CCGCAGGTCCAGTTGCTGTTGTTGCTCTGGTTCTGCAGGTGGCTGGTCAGGGCGGCCATGCTGCAGTCCTTGTACCGGC  1280
1201 GGCGTCCAGGTCAACGACAACAACGAGACCAAGACGTCCACCGACCAGTCCCGCCGGTACGACGTCAGGAACATGGCCG  1280
              R  L  N  W  N  S  N  N  S  Q  N  Q  L  H  S  T  L  A  A  M  S  D  K  Y  R  S
```

Figure 3(continued)

```
            L  D  A  P  L  G  Q  H  G  E  V  E  V  L  G  L  Q  A  C  L  A  V  L  V  Q  V
1281   TCTTGATGCCCCGCTTGGACAGCACGGTGAAGTCGAAGTCCTCGGGCTTCAGGCTTGTCTCGCCGTTCTTGTGCAGGTAG   1360
1281   AGAACTACGGGGCGAACCTGTCGTGCCACTTCAGCTTCAGGAGCCCGAAGTCCGAACAGAGCGGCAAGAACACGTCCATC   1360
            K  I  G  R  K  S  L  V  T  F  D  F  D  E  P  K  L  S  T  E  G  N  K  H  L  Y

V  G  Q  A  A  L  A  S  E  L  Q  A  L  G  A  D  E  V  H  V  E  S  A  G  G  L  A
1361   TTGGCCAGGCTGCTCTTGCTTCTGAACTTCAGGCCCTGGGGGCTGATGAAGTACACGTCGAATCTGCCGGCGGTCTTGCC   1440
1361   AACCGGTCCGACGAGAACGAAGACTTGAAGTCCGGGACCCCCGACTACTTCATGTGCAGCTTAGACGGCCGCCAGAACGG   1440
            N  A  L  S  S  K  S  R  F  K  L  G  Q  P  S  I  F  Y  V  D  F  R  G  A  T  K  G

E  Q  P  L  L  H  H  P  L  P  A  A  G  H  A  L  P  T  L  G  S  G  G  A  E  L
1441   GAACAGCCGCTGCTTCACCACCCGCTCCCAGCCGCAGGGCACGCTCTTCCGACACTCGGTTCCGGCGGTGGCGCCGAACT   1520
1441   CTTGTCGGCGACGAAGTGGTGGGCGAGGGTCGGCGTCCGCTGCGAGAAGGCTGTGAGCCAAGGCCGCCACCGCGGCTTGA   1520
            F  L  R  Q  K  V  V  R  E  W  G  C  P  V  S  K  R  C  E  T  G  A  T  A  G  F  Q

G  A  G  D  R  F  L  Q  Q  G  V  A  L  A  A  P  L  D  H  H  L  F  L  V  L  A
1521   GGCCGCTGGCCATAGGTTCCTGCAGCAGGGGGTTGCACTCGCTGCTCCGCTTGATCATCATCTGTTCCTCGTCCTCGCCC   1600
1521   CCGGCGACCGCTATCCAAGGACGTCGTCCCCCAACGTGAGCGACGAGGCGAACTAGTAGTAGACAAGGAGCAGGAGCGGG   1600
            A  S  A  I  P  E  Q  L  L  P  N  C  E  S  S  R  K  I  M  M  Q  E  E  D  E  G

H  S  F  Q  F  H  G  H  I  F  L  P  Q  V  V  G  G  V  G  H  Q  P  L  A  A  G  H
1601   ACTCTTTCCAGTTCCATGGCCACATCTTGCTTCCGCAGGTCGTTGGGGGGGTCGGGCACCAGCCGCTCGCTGCTGGTCAC   1680
1601   TGAGAAAGGTCAAGGTACCGGTGTAGAAGGAAGGCGTCCAGCAACCCCCCCAGCCCGTGGTCGGCGAGCGACGACCAGTG   1680
            V  R  E  L  E  M  A  V  D  E  K  R  L  D  N  P  P  D  P  V  L  R  E  S  S  T  V

G  R  G  G  S  A  V  A  Q  A  Q  A  F  Q  A  G  G  A  H  G  G  K  L  G  T
1681   GGTAGGGGCGGCTCCGCGGTCGCCCAGGCTCAGGCTTTCCAGGCCGGTGGTGCCCATGGTGGCAAGCTTGGTACC       1755
1681   CCATCCCCGCCGAGGCGCCAGCGGGTCCGAGTCCGAAAGGTCCGGCCACCACGGGTACCACCGTTCGAACCATGG       1755
            T  P  A  A  G  R  D  G  L  S  L  S  E  L  G  T  T  G  M  T  A  L  K  T  G
```

Figure 5

Partial sequence of the pFroup1 vector

Figure 5 (continued)

```
K  T  A  F  Q  V  L  E  E  Y  P  D  S  G  E  N  I  V  D  A  L  A  V  F  L  R  R
AAAAACAGCATTCCAGGTATTAGAAGAATATCCTGATTCAGGTGAAAATATTGTTGATGCGCTGGCAGTGTTCCTGCGCC
TTTTTGTCGTAAGGTCCATAATCTTCTTATAGGACTAAGTCCACTTTTATAACAACTACGCGACCGTCACAAGGACGCGG

H  S  I  P  V  C  N  C  P  F  N  S  D  R  V  F  R  L  A  Q  A  Q  S  R  M
GGTTGCATTCGATTCCTGTTTGTAATTGTCCTTTTAACAGCGATCGCGTATTTCGTCTCGCTCAGGCGCAATCACGAATG
CCAACGTAAGCTAAGGACAAACATTAACAGGAAAATTGTCGCTAGCGCATAAAGCAGAGCGAGTCCGCGTTAGTGCTTAC

N  N  G  L  V  D  A  S  D  F  D  D  E  R  N  G  W  P  V  E  Q  V  W  K  E  M  H
AATAACGGTTTGGTTGATGCGAGTGATTTTGATGACGAGCGTAATGGCTGGCCTGTTGAACAAGTCTGGAAAGAAATGCA
TTATTGCCAAACCAACTACGCTCACTAAAACTACTGCTCGCATTACCGACCGGACAACTTGTTCAGACCTTTCTTTACGT

K  L  L  P  F  S  P  D  S  V  V  T  H  G  D  F  S  L  D  N  L  I  F  D  E  G  K
TAAACTTTTGCCATTCTCACCGGATTCAGTCGTCACTCATGGTGATTTCTCACTTGATAACCTTATTTTTGACGAGGGGA
ATTTGAAAACGGTAAGAGTGGCCTAAGTCAGCAGTGAGTACCACTAAAGAGTGAACTATTGGAATAAAAACTGCTCCCCT

I  G  C  I  D  V  G  R  V  G  I  A  D  R  Y  Q  D  L  A  I  L  W  N  C  L
AATTAATAGGTTGTATTGATGTTGGACGAGTCGGAATCGCAGACCGATACCAGGATCTTGCCATCCTATGGAACTGCCTC
TTAATTATCCAACATAACTACAACCTGCTCAGCCTTAGCGTCTGGCTATGGTCCTAGAACGGTAGGATACCTTGACGGAG

G  E  F  S  P  S  L  Q  K  R  L  F  Q  K  Y  G  I  D  N  P  D  M  N  K  L  Q  F
GGTGAGTTTTCTCCTTCATTACAGAAACGGCTTTTTCAAAAATATGGTATTGATAATCCTGATATGAATAAATTGCAGTT
CCACTCAAAAGAGGAAGTAATGTCTTTGCCGAAAAAGTTTTTATACCATAACTATTAGGACTATACTTATTTAACGTCAA

H  L  M  L  D  E  F  F     S  E  L  V  N  W  L  *  H  W  Q  S  I  T  L  T  *
TCATTTGATGCTCGATGAGTTTTTCTAATCAGAATTGGTTAATTGGTTGTAACACTGGCAGAGCATTACGCTGACTTGAC
AGTAAACTACGAGCTACTCAAAAAGATTAGTCTTAACCAATTAACCAACATTGTGACCGTCTCGTAATGCGACTGAACTG
``` translational coupling

* = Out-of-frame Stopp translational coupling

Western-Blot, α-GFP

SEQUENCE LISTING

<160> NUMBER OF SEQ ID NOS: 21

<210> SEQ ID NO 1
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(735)

<400> SEQUENCE: 1

```
gag ctc aag ctt gta cag ttc atc cat gcc cag ggt aat acc agc ggc     48
Glu Leu Lys Leu Val Gln Phe Ile His Ala Gln Gly Asn Thr Ser Gly
1               5                   10                  15 ggt cac gaa ttc cag cag cac cat gtg atc acg ttt ttc gtt cgg atc     96
Gly His Glu Phe Gln Gln His His Val Ile Thr Phe Phe Val Arg Ile
            20                  25                  30 ttt gct cag ggc gct ctg ggt gct cag gta gtg gtt atc cgg cag cag    144
Phe Ala Gln Gly Ala Leu Gly Ala Gln Val Val Val Ile Arg Gln Gln
        35                  40                  45 cac cgg gcc atc acc aat cgg ggt gtt ctg ctg gta gtg atc ggc cag    192
His Arg Ala Ile Thr Asn Arg Gly Val Leu Leu Val Val Ile Gly Gln
    50                  55                  60 ctg cac gct gcc atc ttc gat gtt gtg gcg gat ttt gaa gtt cac ttt    240
Leu His Ala Ala Ile Phe Asp Val Val Ala Asp Phe Glu Val His Phe
65                  70                  75                  80 gat gcc gtt ttt ctg ttt atc ggc cat gat gta cac gtt gtg gct gtt    288
Asp Ala Val Phe Leu Phe Ile Gly His Asp Val His Val Val Ala Val
                85                  90                  95 gta gtt gta ttc cag ttt gtg gcc cag gat gtt acc gtc ctc ttt aaa    336
Val Val Val Phe Gln Phe Val Ala Gln Asp Val Thr Val Leu Phe Lys
            100                 105                 110 gtc gat gcc ttt cag ttc gat acg gtt cac cag ggt atc gcc ttc gaa    384
Val Asp Ala Phe Gln Phe Asp Thr Val His Gln Gly Ile Ala Phe Glu
        115                 120                 125 ttt cac ttc ggc acg ggt ttt gta gtt gcc atc atc ttt gaa gaa aat    432
Phe His Phe Gly Thr Gly Phe Val Val Ala Ile Ile Phe Glu Glu Asn
    130                 135                 140 ggt acg ttc ctg cac gta gcc ttc cgg cat ggc gct ttt gaa gaa atc    480
Gly Thr Phe Leu His Val Ala Phe Arg His Gly Ala Phe Glu Glu Ile
145                 150                 155                 160 gtg ctg ttt cat gtg atc cgg gta gcg aga gaa gca ctg cac gcc gta    528
Val Leu Phe His Val Ile Arg Val Ala Arg Glu Ala Leu His Ala Val
                165                 170                 175 ggt cag ggt ggt cac cag ggt cgg cca cgg cac cgg cag ttt gcc ggt    576
Gly Gln Gly Gly His Gln Gly Arg Pro Arg His Arg Gln Phe Ala Gly
            180                 185                 190 ggt aca gat gaa ttt cag ggt cag ttt gcc gta ggt ggc atc acc ttc    624
Gly Thr Asp Glu Phe Gln Gly Gln Phe Ala Val Gly Gly Ile Thr Phe
        195                 200                 205 acc ttc gcc gga cac gct gaa ttt gtg gcc gtt cac atc gcc atc cag    672
Thr Phe Ala Gly His Ala Glu Phe Val Ala Val His Ile Ala Ile Gln
    210                 215                 220 ttc cac cag aat cgg cac cac gcc ggt gaa cag ttc ttc gcc ttt gga    720
Phe His Gln Asn Arg His His Ala Gly Glu Gln Phe Phe Ala Phe Gly
225                 230                 235                 240 cac cat atg ggt acc                                                735
His His Met Gly Thr
                245
```

<210> SEQ ID NO 2
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Glu Leu Lys Leu Val Gln Phe Ile His Ala Gln Gly Asn Thr Ser Gly
1               5                   10                  15

Gly His Glu Phe Gln Gln His His Val Ile Thr Phe Phe Val Arg Ile
            20                  25                  30

Phe Ala Gln Gly Ala Leu Gly Ala Gln Val Val Ile Arg Gln Gln
        35                  40                  45

His Arg Ala Ile Thr Asn Arg Gly Val Leu Leu Val Val Ile Gly Gln
    50                  55                  60

Leu His Ala Ala Ile Phe Asp Val Val Ala Asp Phe Glu Val His Phe
65                  70                  75                  80

Asp Ala Val Phe Leu Phe Ile Gly His Asp Val His Val Val Ala Val
                85                  90                  95

Val Val Val Phe Gln Phe Val Ala Gln Asp Val Thr Val Leu Phe Lys
            100                 105                 110

Val Asp Ala Phe Gln Phe Asp Thr Val His Gln Gly Ile Ala Phe Glu
        115                 120                 125

Phe His Phe Gly Thr Gly Phe Val Val Ala Ile Ile Phe Glu Glu Asn
    130                 135                 140

Gly Thr Phe Leu His Val Ala Phe Arg His Gly Ala Phe Glu Glu Ile
145                 150                 155                 160

Val Leu Phe His Val Ile Arg Val Ala Arg Glu Ala Leu His Ala Val
                165                 170                 175

Gly Gln Gly Gly His Gln Gly Arg Pro Arg His Arg Gln Phe Ala Gly
            180                 185                 190

Gly Thr Asp Glu Phe Gln Gly Gln Phe Ala Val Gly Gly Ile Thr Phe
        195                 200                 205

Thr Phe Ala Gly His Ala Glu Phe Val Ala Val His Ile Ala Ile Gln
    210                 215                 220

Phe His Gln Asn Arg His His Ala Gly Glu Gln Phe Phe Ala Phe Gly
225                 230                 235                 240

His His Met Gly Thr
                245
```

<210> SEQ ID NO 3
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(735)

<400> SEQUENCE: 3

```
ggt acc cat atg gtg tcc aaa ggc gaa gaa ctg ttc acc ggc gtg gtg      48
Gly Thr His Met Val Ser Lys Gly Glu Glu Leu Phe Thr Gly Val Val
1               5                   10                  15 ccg att ctg gtg gaa ctg gat ggc gat gtg aac ggc cac aaa ttc agc      96
```

```
                Pro Ile Leu Val Glu Leu Asp Gly Asp Val Asn Gly His Lys Phe Ser
                                 20                  25                  30 gtg tcc ggc gaa ggt gaa ggt gat gcc acc tac ggc aaa ctg acc ctg              144
Val Ser Gly Glu Gly Glu Gly Asp Ala Thr Tyr Gly Lys Leu Thr Leu
             35                  40                  45 aaa ttc atc tgt acc acc ggc aaa ctg ccg gtg ccg tgg ccg acc ctg              192
Lys Phe Ile Cys Thr Thr Gly Lys Leu Pro Val Pro Trp Pro Thr Leu
 50                  55                  60 gtg acc acc ctg acc tac ggc gtg cag tgc ttc tct cgc tac ccg gat              240
Val Thr Thr Leu Thr Tyr Gly Val Gln Cys Phe Ser Arg Tyr Pro Asp
 65                  70                  75                  80 cac atg aaa cag cac gat ttc ttc aaa agc gcc atg ccg gaa ggc tac              288
His Met Lys Gln His Asp Phe Phe Lys Ser Ala Met Pro Glu Gly Tyr
                 85                  90                  95 gtg cag gaa cgt acc att ttc ttc aaa gat gat ggc aac tac aaa acc              336
Val Gln Glu Arg Thr Ile Phe Phe Lys Asp Asp Gly Asn Tyr Lys Thr
            100                 105                 110 cgt gcc gaa gtg aaa ttc gaa ggc gat acc ctg gtg aac cgt atc gaa              384
Arg Ala Glu Val Lys Phe Glu Gly Asp Thr Leu Val Asn Arg Ile Glu
            115                 120                 125 ctg aaa ggc atc gac ttt aaa gag gac ggt aac atc ctg ggc cac aaa              432
Leu Lys Gly Ile Asp Phe Lys Glu Asp Gly Asn Ile Leu Gly His Lys
        130                 135                 140 ctg gaa tac aac tac aac agc cac aac gtg tac atc atg gcc gat aaa              480
Leu Glu Tyr Asn Tyr Asn Ser His Asn Val Tyr Ile Met Ala Asp Lys
145                 150                 155                 160 cag aaa aac ggc atc aaa gtg aac ttc aaa atc cgc cac aac atc gaa              528
Gln Lys Asn Gly Ile Lys Val Asn Phe Lys Ile Arg His Asn Ile Glu
                165                 170                 175 gat ggc agc gtg cag ctg gcc gat cac tac cag cag aac acc ccg att              576
Asp Gly Ser Val Gln Leu Ala Asp His Tyr Gln Gln Asn Thr Pro Ile
            180                 185                 190 ggt gat ggc ccg gtg ctg ctg ccg gat aac cac tac ctg agc acc cag              624
Gly Asp Gly Pro Val Leu Leu Pro Asp Asn His Tyr Leu Ser Thr Gln
            195                 200                 205 agc gcc ctg agc aaa gat ccg aac gaa aaa cgt gat cac atg gtg ctg              672
Ser Ala Leu Ser Lys Asp Pro Asn Glu Lys Arg Asp His Met Val Leu
        210                 215                 220 ctg gaa ttc gtg acc gcc gct ggt att acc ctg ggc atg gat gaa ctg              720
Leu Glu Phe Val Thr Ala Ala Gly Ile Thr Leu Gly Met Asp Glu Leu
225                 230                 235                 240 tac aag ctt gag ctc                                                          735
Tyr Lys Leu Glu Leu
                245

<210> SEQ ID NO 4
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Thr His Met Val Ser Lys Gly Glu Glu Leu Phe Thr Gly Val Val
1               5                   10                  15

Pro Ile Leu Val Glu Leu Asp Gly Asp Val Asn Gly His Lys Phe Ser
                 20                  25                  30

Val Ser Gly Glu Gly Glu Gly Asp Ala Thr Tyr Gly Lys Leu Thr Leu
             35                  40                  45
```

```
Lys Phe Ile Cys Thr Thr Gly Lys Leu Pro Val Pro Trp Pro Thr Leu
    50                  55                  60

Val Thr Thr Leu Thr Tyr Gly Val Gln Cys Phe Ser Arg Tyr Pro Asp
65                  70                  75                  80

His Met Lys Gln His Asp Phe Phe Lys Ser Ala Met Pro Glu Gly Tyr
                85                  90                  95

Val Gln Glu Arg Thr Ile Phe Phe Lys Asp Asp Gly Asn Tyr Lys Thr
            100                 105                 110

Arg Ala Glu Val Lys Phe Glu Gly Asp Thr Leu Val Asn Arg Ile Glu
        115                 120                 125

Leu Lys Gly Ile Asp Phe Lys Glu Asp Gly Asn Ile Leu Gly His Lys
    130                 135                 140

Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr Leu Gly Met Asp Glu Leu
225                 230                 235                 240

Tyr Lys Leu Glu Leu
                245

<210> SEQ ID NO 5
<211> LENGTH: 1398
<212> TYPE: DNA
<213> ORGANISM: Influenza virus
<220> FEATURE:
<221> NAME/KEY: CDS
<222> LOCATION: (1)..(1398)

<400> SEQUENCE: 5 gag ctc acg gct gct gcc tta tta ttt atc aat ggt aaa cgg cag ttc    48
Glu Leu Thr Ala Ala Ala Leu Leu Phe Ile Asn Gly Lys Arg Gln Phe
1               5                   10                  15 cgc gcc atc cgg cca gct cca gct cac ggt atc gct gtt cac gcc gca    96
Arg Ala Ile Arg Pro Ala Pro Ala His Gly Ile Ala Val His Ala Ala
            20                  25                  30 aaa gct aat gct gct gcc gct ggt cca aat ggt gct ttc ttt cgg acg   144
Lys Ala Asn Ala Ala Ala Ala Gly Pro Asn Gly Ala Phe Phe Arg Thr
        35                  40                  45 gcc acg aat cag ttc cac cca aaa gca cgg acg aat gca atc cag gcc   192
Ala Thr Asn Gln Phe His Pro Lys Ala Arg Thr Asn Ala Ile Gln Ala
    50                  55                  60 ggt cag ttc cgg atg ctg cac aaa gct gcc gct ata gcc gct cca atc   240
Gly Gln Phe Arg Met Leu His Lys Ala Ala Ala Ile Ala Ala Pro Ile
65                  70                  75                  80 ggt aat cgc cac aat atc ctg ttt cac gct aaa gct gct atc ggt gcc   288
Gly Asn Arg His Asn Ile Leu Phe His Ala Lys Ala Ala Ile Gly Ala
                85                  90                  95 ggt cca gcc gtt cgg atc cca aat cat ttc aaa gcc gct acg gct gtt   336
Gly Pro Ala Val Arg Ile Pro Asn His Phe Lys Ala Ala Thr Ala Val
            100                 105                 110 ggt gct ttt ggt acg gcc aat cca cac gcc atc gcc ata ttt aaa gct   384
```

```
Gly Ala Phe Gly Thr Ala Asn Pro His Ala Ile Ala Ile Phe Lys Ala
            115                 120                 125 aaa gcc ttt cac gcc ata cgc gcc gtt cgg gct cat cgg gcc gca gct       432
Lys Ala Phe His Ala Ile Arg Ala Val Arg Ala His Arg Ala Ala Ala
        130                 135                 140 gcc ggt gcc atc gtt cgg acg cgg gtt atc gcc aaa cac gcc gct gca       480
Ala Gly Ala Ile Val Arg Thr Arg Val Ile Ala Lys His Ala Ala Ala
145                 150                 155                 160 aat ata gcc aat ctg ata ttc cag gtt ctg gtt aaa gct cac cca cgg       528
Asn Ile Ala Asn Leu Ile Phe Gln Val Leu Val Lys Ala His Pro Arg
                165                 170                 175 acg gtt gct gcc atg cca gtt atc acg gca cac gca ggt aat ttc gcc       576
Thr Val Ala Ala Met Pro Val Ile Thr Ala His Ala Gly Asn Phe Ala
            180                 185                 190 cgc atc cgg ata gca gct gca ttc ttc ata atg ata gtt cgg cgc atc       624
Arg Ile Arg Ile Ala Ala Ala Phe Phe Ile Met Ile Val Arg Arg Ile
        195                 200                 205 cag ttc cac gct ttt cac cac ttt gcc ttt ttc cat ttt aaa aat ttt       672
Gln Phe His Ala Phe His His Phe Ala Phe Phe His Phe Lys Asn Phe
210                 215                 220 ata gct cgc ctg gcc gtt gct cgg gcc atc ggt cat cac ggt aaa gca       720
Ile Ala Arg Leu Ala Val Ala Arg Ala Ile Gly His His Gly Lys Ala
225                 230                 235                 240 gct gcc gtt cac gca cgc gca ttc gct ttc ctg ggt acg cag aat gtt       768
Ala Ala Val His Ala Arg Ala Phe Ala Phe Leu Gly Thr Gln Asn Val
                245                 250                 255 gtt acg cca gct ttt aat ggt atc ggt aat aat gcc gtt ata ttt cag       816
Val Thr Pro Ala Phe Asn Gly Ile Gly Asn Asn Ala Val Ile Phe Gln
            260                 265                 270 cac cgc cac cgc gcc gtt atc cgg gcc gct aat gcc aat ggt cag cca       864
His Arg His Arg Ala Val Ile Arg Ala Ala Asn Ala Asn Gly Gln Pro
        275                 280                 285 gct ggt gcc atc atg gca cgc gct cgc gct cca cgc cac gct ttc aaa       912
Ala Gly Ala Ile Met Ala Arg Ala Arg Ala Pro Arg His Ala Phe Lys
290                 295                 300 acg gct gtt ata cgg gct cgg cgc ttc gcc cac cgg gca gct cat cag       960
Thr Ala Val Ile Arg Ala Arg Arg Phe Ala His Arg Ala Ala His Gln
305                 310                 315                 320 ggt acg atg cgg gct acg atc ttt cac ggt gcc gtt gct atg ttt atc      1008
Gly Thr Met Arg Ala Thr Ile Phe His Gly Ala Val Ala Met Phe Ile
                325                 330                 335 gtt cag cag cgc gcc ctg ggt cag aaa aaa ggt acg gca ttc cag atg      1056
Val Gln Gln Arg Ala Leu Gly Gln Lys Lys Gly Thr Ala Phe Gln Met
            340                 345                 350 gct gca gct aat aaa cgg ttc acg aat cac aaa cac atc gcc ttt gct      1104
Ala Ala Ala Asn Lys Arg Phe Thr Asn His Lys His Ile Ala Phe Ala
        355                 360                 365 gcc aat acg aat gtt gtt atc ttt gct atg cac cgc cca gcc acg aat      1152
Ala Asn Thr Asn Val Val Ile Phe Ala Met His Arg Pro Ala Thr Asn
370                 375                 380 cgg gca cag gct gct gtt gcc cgc cag ggt cac gct cgc cac cgc ttt      1200
Arg Ala Gln Ala Ala Val Ala Arg Gln Gly His Ala Arg His Arg Phe
385                 390                 395                 400 ttc ggt cag cgg gtt ggt gtt gct aat gct ttc cgc ctg atg ctg gct      1248
Phe Gly Gln Arg Val Gly Val Ala Asn Ala Phe Arg Leu Met Leu Ala
                405                 410                 415 gcc ggt ctg aat gct atg gct cac cca aat gct aat cat gtt gcc aat      1296
Ala Gly Leu Asn Ala Met Ala His Pro Asn Ala Asn His Val Ala Asn
            420                 425                 430
```

```
ctg cag cat cag gct cac ggt gcc aat cac cat gca aat gct gcc aat    1344
Leu Gln His Gln Ala His Gly Ala Asn His His Ala Asn Ala Ala Asn
    435                 440                 445 ggt aat aat ttt ctg gtt cgg gtt cat ggt cgc acg gcc acg ata acg    1392
Gly Asn Asn Phe Leu Val Arg Val His Gly Arg Thr Ala Thr Ile Thr
450                 455                 460 ggt acc                                                             1398
Gly Thr
465

<210> SEQ ID NO 6
<211> LENGTH: 466
<212> TYPE: PRT
<213> ORGANISM: Influenza virus

<400> SEQUENCE: 6

Glu Leu Thr Ala Ala Leu Leu Phe Ile Asn Gly Lys Arg Gln Phe
1               5                   10                  15

Arg Ala Ile Arg Pro Ala Pro Ala His Gly Ile Ala Val His Ala Ala
                20                  25                  30

Lys Ala Asn Ala Ala Ala Ala Gly Pro Asn Gly Ala Phe Phe Arg Thr
            35                  40                  45

Ala Thr Asn Gln Phe His Pro Lys Ala Arg Thr Asn Ala Ile Gln Ala
        50                  55                  60

Gly Gln Phe Arg Met Leu His Lys Ala Ala Ile Ala Ala Pro Ile
65                  70                  75                  80

Gly Asn Arg His Asn Ile Leu Phe His Ala Lys Ala Ala Ile Gly Ala
                85                  90                  95

Gly Pro Ala Val Arg Ile Pro Asn His Phe Lys Ala Ala Thr Ala Val
            100                 105                 110

Gly Ala Phe Gly Thr Ala Asn Pro His Ala Ile Ala Ile Phe Lys Ala
        115                 120                 125

Lys Ala Phe His Ala Ile Arg Ala Val Arg Ala His Arg Ala Ala Ala
    130                 135                 140

Ala Gly Ala Ile Val Arg Thr Arg Val Ile Ala Lys His Ala Ala
145                 150                 155                 160

Asn Ile Ala Asn Leu Ile Phe Gln Val Leu Val Lys Ala His Pro Arg
                165                 170                 175

Thr Val Ala Ala Met Pro Val Ile Thr Ala His Ala Gly Asn Phe Ala
            180                 185                 190

Arg Ile Arg Ile Ala Ala Ala Phe Phe Ile Met Ile Val Arg Arg Ile
        195                 200                 205

Gln Phe His Ala Phe His His Phe Ala Phe Phe His Phe Lys Asn Phe
    210                 215                 220

Ile Ala Arg Leu Ala Val Ala Arg Ala Ile Gly His His Gly Lys Ala
225                 230                 235                 240

Ala Ala Val His Ala Arg Ala Phe Ala Phe Leu Gly Thr Gln Asn Val
                245                 250                 255

Val Thr Pro Ala Phe Asn Gly Ile Gly Asn Asn Ala Val Ile Phe Gln
            260                 265                 270

His Arg His Arg Ala Val Ile Arg Ala Ala Asn Ala Asn Gly Gln Pro
        275                 280                 285

Ala Gly Ala Ile Met Ala Arg Ala Arg Ala Pro Arg His Ala Phe Lys
    290                 295                 300

Thr Ala Val Ile Arg Ala Arg Arg Phe Ala His Arg Ala Ala His Gln
305                 310                 315                 320
```

```
Gly Thr Met Arg Ala Thr Ile Phe His Gly Ala Val Ala Met Phe Ile
                325                 330                 335

Val Gln Gln Arg Ala Leu Gly Gln Lys Lys Gly Thr Ala Phe Gln Met
            340                 345                 350

Ala Ala Ala Asn Lys Arg Phe Thr Asn His Lys His Ile Ala Phe Ala
        355                 360                 365

Ala Asn Thr Asn Val Val Ile Phe Ala Met His Arg Pro Ala Thr Asn
    370                 375                 380

Arg Ala Gln Ala Ala Val Ala Arg Gln Gly His Ala Arg His Arg Phe
385                 390                 395                 400

Phe Gly Gln Arg Val Gly Val Ala Asn Ala Phe Arg Leu Met Leu Ala
                405                 410                 415

Ala Gly Leu Asn Ala Met Ala His Pro Asn Ala Asn His Val Ala Asn
            420                 425                 430

Leu Gln His Gln Ala His Gly Ala Asn His His Ala Asn Ala Ala Asn
        435                 440                 445

Gly Asn Asn Phe Leu Val Arg Val His Gly Arg Thr Ala Thr Ile Thr
    450                 455                 460

Gly Thr
465

<210> SEQ ID NO 7
<211> LENGTH: 1398
<212> TYPE: DNA
<213> ORGANISM: Influenza virus
<220> FEATURE:
<221> NAME/KEY: CDS
<222> LOCATION: (1)..(1374)
<220> FEATURE:
<221> NAME/KEY: CDS
<222> LOCATION: (1381)..(1398)

<400> SEQUENCE: 7 ggt acc cgt tat cgt ggc cgt gcg acc atg aac ccg aac cag aaa att      48
Gly Thr Arg Tyr Arg Gly Arg Ala Thr Met Asn Pro Asn Gln Lys Ile
1               5                   10                  15 att acc att ggc agc att tgc atg gtg att ggc acc gtg agc ctg atg      96
Ile Thr Ile Gly Ser Ile Cys Met Val Ile Gly Thr Val Ser Leu Met
            20                  25                  30 ctg cag att ggc aac atg att agc att tgg gtg agc cat agc att cag     144
Leu Gln Ile Gly Asn Met Ile Ser Ile Trp Val Ser His Ser Ile Gln
        35                  40                  45 acc ggc agc cag cat cag gcg gaa agc att agc aac acc aac ccg ctg     192
Thr Gly Ser Gln His Gln Ala Glu Ser Ile Ser Asn Thr Asn Pro Leu
    50                  55                  60 acc gaa aaa gcg gtg gcg agc gtg acc ctg gcg ggc aac agc agc ctg     240
Thr Glu Lys Ala Val Ala Ser Val Thr Leu Ala Gly Asn Ser Ser Leu
65                  70                  75                  80 tgc ccg att cgt ggc tgg gcg gtg cat agc aaa gat aac aac att cgt     288
Cys Pro Ile Arg Gly Trp Ala Val His Ser Lys Asp Asn Asn Ile Arg
                85                  90                  95 att ggc agc aaa ggc gat gtg ttt gtg att cgt gaa ccg ttt att agc     336
Ile Gly Ser Lys Gly Asp Val Phe Val Ile Arg Glu Pro Phe Ile Ser
            100                 105                 110 tgc agc cat ctg gaa tgc cgt acc ttt ttt ctg acc cag ggc gcg ctg     384
Cys Ser His Leu Glu Cys Arg Thr Phe Phe Leu Thr Gln Gly Ala Leu
        115                 120                 125 ctg aac gat aaa cat agc aac ggc acc gtg aaa gat cgt agc ccg cat     432
Leu Asn Asp Lys His Ser Asn Gly Thr Val Lys Asp Arg Ser Pro His
```

-continued

```
               130                 135                 140
cgt acc ctg atg agc tgc ccg gtg ggc gaa gcg ccg agc ccg tat aac     480
Arg Thr Leu Met Ser Cys Pro Val Gly Glu Ala Pro Ser Pro Tyr Asn
145                 150                 155                 160 agc cgt ttt gaa agc gtg gcg tgg agc gcg agc gcg tgc cat gat ggc     528
Ser Arg Phe Glu Ser Val Ala Trp Ser Ala Ser Ala Cys His Asp Gly
                    165                 170                 175 acc agc tgg ctg acc att ggc att agc ggc ccg gat aac ggc gcg gtg     576
Thr Ser Trp Leu Thr Ile Gly Ile Ser Gly Pro Asp Asn Gly Ala Val
            180                 185                 190 gcg gtg ctg aaa tat aac ggc att att acc gat acc att aaa agc tgg     624
Ala Val Leu Lys Tyr Asn Gly Ile Ile Thr Asp Thr Ile Lys Ser Trp
        195                 200                 205 cgt aac aac att ctg cgt acc cag gaa agc gaa tgc gcg tgc gtg aac     672
Arg Asn Asn Ile Leu Arg Thr Gln Glu Ser Glu Cys Ala Cys Val Asn
210                 215                 220 ggc agc tgc ttt acc gtg atg acc gat ggc ccg agc aac ggc cag gcg     720
Gly Ser Cys Phe Thr Val Met Thr Asp Gly Pro Ser Asn Gly Gln Ala
225                 230                 235                 240 agc tat aaa att ttt aaa atg gaa aaa ggc aaa gtg gtg aaa agc gtg     768
Ser Tyr Lys Ile Phe Lys Met Glu Lys Gly Lys Val Val Lys Ser Val
                    245                 250                 255 gaa ctg gat gcg ccg aac tat cat tat gaa gaa tgc agc tgc tat ccg     816
Glu Leu Asp Ala Pro Asn Tyr His Tyr Glu Glu Cys Ser Cys Tyr Pro
            260                 265                 270 gat gcg ggc gaa att acc tgc gtg tgc cgt gat aac tgg cat ggc agc     864
Asp Ala Gly Glu Ile Thr Cys Val Cys Arg Asp Asn Trp His Gly Ser
        275                 280                 285 aac cgt ccg tgg gtg agc ttt aac cag aac ctg gaa tat cag att ggc     912
Asn Arg Pro Trp Val Ser Phe Asn Gln Asn Leu Glu Tyr Gln Ile Gly
290                 295                 300 tat att tgc agc ggc gtg ttt ggc gat aac ccg cgt ccg aac gat ggc     960
Tyr Ile Cys Ser Gly Val Phe Gly Asp Asn Pro Arg Pro Asn Asp Gly
305                 310                 315                 320 acc ggc agc tgc ggc ccg atg agc ccg aac ggc gcg tat ggc gtg aaa    1008
Thr Gly Ser Cys Gly Pro Met Ser Pro Asn Gly Ala Tyr Gly Val Lys
                    325                 330                 335 ggc ttt agc ttt aaa tat ggc gat ggc gtg tgg att ggc cgt acc aaa    1056
Gly Phe Ser Phe Lys Tyr Gly Asp Gly Val Trp Ile Gly Arg Thr Lys
            340                 345                 350 agc acc aac agc cgt agc ggc ttt gaa atg att tgg gat ccg aac ggc    1104
Ser Thr Asn Ser Arg Ser Gly Phe Glu Met Ile Trp Asp Pro Asn Gly
        355                 360                 365 tgg acc ggc acc gat agc agc ttt agc gtg aaa cag gat att gtg gcg    1152
Trp Thr Gly Thr Asp Ser Ser Phe Ser Val Lys Gln Asp Ile Val Ala
370                 375                 380 att acc gat tgg agc ggc tat agc ggc agc ttt gtg cag cat ccg gaa    1200
Ile Thr Asp Trp Ser Gly Tyr Ser Gly Ser Phe Val Gln His Pro Glu
385                 390                 395                 400 ctg acc ggc ctg gat tgc att cgt ccg tgc ttt tgg gtg gaa ctg att    1248
Leu Thr Gly Leu Asp Cys Ile Arg Pro Cys Phe Trp Val Glu Leu Ile
                    405                 410                 415 cgt ggc cgt ccg aaa gaa agc acc att tgg acc agc ggc agc agc att    1296
Arg Gly Arg Pro Lys Glu Ser Thr Ile Trp Thr Ser Gly Ser Ser Ile
            420                 425                 430 agc ttt tgc ggc gtg aac agc gat acc gtg agc tgg agc tgg ccg gat    1344
Ser Phe Cys Gly Val Asn Ser Asp Thr Val Ser Trp Ser Trp Pro Asp
        435                 440                 445 ggc gcg gaa ctg ccg ttt acc att gat aaa taataa ggc agc agc cgt    1392
```

```
Gly Ala Glu Leu Pro Phe Thr Ile Asp Lys     Gly Ser Ser Arg
    450                 455                 460 gag ctc                                                                 1398
Glu Leu <210> SEQ ID NO 8
<211> LENGTH: 458
<212> TYPE: PRT
<213> ORGANISM: Influenza virus

<400> SEQUENCE: 8

Gly Thr Arg Tyr Arg Gly Arg Ala Thr Met Asn Pro Asn Gln Lys Ile
1               5                   10                  15

Ile Thr Ile Gly Ser Ile Cys Met Val Ile Gly Thr Val Ser Leu Met
            20                  25                  30

Leu Gln Ile Gly Asn Met Ile Ser Ile Trp Val Ser His Ser Ile Gln
        35                  40                  45

Thr Gly Ser Gln His Gln Ala Glu Ser Ile Ser Asn Thr Asn Pro Leu
    50                  55                  60

Thr Glu Lys Ala Val Ala Ser Val Thr Leu Ala Gly Asn Ser Ser Leu
65                  70                  75                  80

Cys Pro Ile Arg Gly Trp Ala Val His Ser Lys Asp Asn Asn Ile Arg
                85                  90                  95

Ile Gly Ser Lys Gly Asp Val Phe Val Ile Arg Glu Pro Phe Ile Ser
            100                 105                 110

Cys Ser His Leu Glu Cys Arg Thr Phe Phe Leu Thr Gln Gly Ala Leu
        115                 120                 125

Leu Asn Asp Lys His Ser Asn Gly Thr Val Lys Asp Arg Ser Pro His
    130                 135                 140

Arg Thr Leu Met Ser Cys Pro Val Gly Glu Ala Pro Ser Pro Tyr Asn
145                 150                 155                 160

Ser Arg Phe Glu Ser Val Ala Trp Ser Ala Ser Ala Cys His Asp Gly
                165                 170                 175

Thr Ser Trp Leu Thr Ile Gly Ile Ser Gly Pro Asp Asn Gly Ala Val
            180                 185                 190

Ala Val Leu Lys Tyr Asn Gly Ile Ile Thr Asp Thr Ile Lys Ser Trp
        195                 200                 205

Arg Asn Asn Ile Leu Arg Thr Gln Glu Ser Glu Cys Ala Cys Val Asn
    210                 215                 220

Gly Ser Cys Phe Thr Val Met Thr Asp Gly Pro Ser Asn Gly Gln Ala
225                 230                 235                 240

Ser Tyr Lys Ile Phe Lys Met Glu Lys Gly Lys Val Val Lys Ser Val
                245                 250                 255

Glu Leu Asp Ala Pro Asn Tyr His Tyr Glu Glu Cys Ser Cys Tyr Pro
            260                 265                 270

Asp Ala Gly Glu Ile Thr Cys Val Cys Arg Asp Asn Trp His Gly Ser
        275                 280                 285

Asn Arg Pro Trp Val Ser Phe Asn Gln Asn Leu Glu Tyr Gln Ile Gly
    290                 295                 300

Tyr Ile Cys Ser Gly Val Phe Gly Asp Asn Pro Arg Pro Asn Asp Gly
305                 310                 315                 320

Thr Gly Ser Cys Gly Pro Met Ser Pro Asn Gly Ala Tyr Gly Val Lys
                325                 330                 335

Gly Phe Ser Phe Lys Tyr Gly Asp Gly Val Trp Ile Gly Arg Thr Lys
            340                 345                 350
```

```
Ser Thr Asn Ser Arg Ser Gly Phe Glu Met Ile Trp Asp Pro Asn Gly
        355                 360                 365

Trp Thr Gly Thr Asp Ser Ser Phe Ser Val Lys Gln Asp Ile Val Ala
370                 375                 380

Ile Thr Asp Trp Ser Gly Tyr Ser Gly Ser Phe Val Gln His Pro Glu
385                 390                 395                 400

Leu Thr Gly Leu Asp Cys Ile Arg Pro Cys Phe Trp Val Glu Leu Ile
                405                 410                 415

Arg Gly Arg Pro Lys Glu Ser Thr Ile Trp Thr Ser Gly Ser Ser Ile
                420                 425                 430

Ser Phe Cys Gly Val Asn Ser Asp Thr Val Ser Trp Ser Trp Pro Asp
                435                 440                 445

Gly Ala Glu Leu Pro Phe Thr Ile Asp Lys
        450                 455

<210> SEQ ID NO 9
<211> LENGTH: 1755
<212> TYPE: DNA
<213> ORGANISM: Homo sapiens
<220> FEATURE:
<221> NAME/KEY: CDS
<222> LOCATION: (1)..(1755)

<400> SEQUENCE: 9 gag ctc cag tta tta gct cag gct cag ttt ttc atg gtt ttc cca cag        48
Glu Leu Gln Leu Leu Ala Gln Ala Gln Phe Phe Met Val Phe Pro Gln
1               5                   10                  15 cca atc atg ata ttt gtt cag ttt atg atc ttc cgg atg cac ctg ttt        96
Pro Ile Met Ile Phe Val Gln Phe Met Ile Phe Arg Met His Leu Phe
                20                  25                  30 cca ttc gtt cac gca aaa aat acg ata gct atc gtt gcc ata ttt gcc       144
Pro Phe Val His Ala Lys Asn Thr Ile Ala Ile Val Ala Ile Phe Ala
            35                  40                  45 aat gcc atg cag ttc aat cgg ata ttt cca ctg ttt ggt cag ata ttc       192
Asn Ala Met Gln Phe Asn Arg Ile Phe Pro Leu Phe Gly Gln Ile Phe
        50                  55                  60 atc gct aaa ttt cac aat ggt ttt cgc acg cag atc ata cag gcc cag       240
Ile Ala Lys Phe His Asn Gly Phe Arg Thr Gln Ile Ile Gln Ala Gln
65                  70                  75                  80 cgg ttt cag cag ttc gct cac atc acg cca atc cgc ggt acg cgc cac       288
Arg Phe Gln Gln Phe Ala His Ile Thr Pro Ile Arg Gly Thr Arg His
                85                  90                  95 ttc cgc gct cgg ata ttt ttc cag aaa ttt cca cag cac cgg aat cgc       336
Phe Arg Ala Arg Ile Phe Phe Gln Lys Phe Pro Gln His Arg Asn Arg
            100                 105                 110 cat ttt gcc gct ggt acg gtt cag aaa aat ggt cgc aat cag cag ttt       384
His Phe Ala Ala Gly Thr Val Gln Lys Asn Gly Arg Asn Gln Gln Phe
        115                 120                 125 cca cgg atc atg aaa cag ggt ttc ctg cac cag gtt aaa cgg gct acg       432
Pro Arg Ile Met Lys Gln Gly Phe Leu His Gln Val Lys Arg Ala Thr
    130                 135                 140 cgg cgg ggt cca ttt ttt aaa cgc ttt acg acg cgg ggt cag cgc             480
Arg Arg Gly Pro Phe Phe Lys Arg Phe Thr Thr Arg Arg Ala Gln Arg
145                 150                 155                 160 ttc ttt gtt ata ttt gct gct aaa ata cag gct ggt ttt acg acg ttc       528
Phe Phe Val Ile Phe Ala Ala Lys Ile Gln Ala Gly Phe Thr Thr Phe
                165                 170                 175 aat ctg ggt acg cgg aat ggt atc ttc ggt aaa atc ttt acg ggt cgg       576
Asn Leu Gly Thr Arg Asn Gly Ile Phe Gly Lys Ile Phe Thr Gly Arg
```

```
                180             185             190
gct gca gtt gtt atc cat ttc gct gcc acg ttt cag aat atc ggt atg    624
Ala Ala Val Val Ile His Phe Ala Ala Thr Phe Gln Asn Ile Gly Met
        195                 200                 205 cag atg ttc ttt acg ttc cac cac ttc cac ttt ggt gcc aat ttc ttc    672
Gln Met Phe Phe Thr Phe His His Phe His Phe Gly Ala Asn Phe Phe
210                 215                 220 gct ttc cag aaa ggt atc ttc ata ttt ttc gtt atg ttc gct atc ttt    720
Ala Phe Gln Lys Gly Ile Phe Ile Phe Phe Val Met Phe Ala Ile Phe
225                 230                 235                 240 cgc gct gca aaa ttt gtt aat aat gcc gct ggt ttt ctg ttc gct gca    768
Arg Ala Ala Lys Phe Val Asn Asn Ala Ala Gly Phe Leu Phe Ala Ala
                245                 250                 255 aaa gtt gct gcc gct gct cag gct acg ttc ttt ttt ttt cac cag gct    816
Lys Val Ala Ala Ala Ala Gln Ala Thr Phe Phe Phe Phe His Gln Ala
            260                 265                 270 gtt ttc ttc gct ggt cac gct cag ggt ttc gcc gca cgc gcc cgc atc    864
Val Phe Phe Ala Gly His Ala Gln Gly Phe Ala Ala Arg Ala Arg Ile
        275                 280                 285 gct aat gca cac ggt acg atc cag ctg gct ttt ctg cgc cac cgg ttc    912
Ala Asn Ala His Gly Thr Ile Gln Leu Ala Phe Leu Arg His Arg Phe
290                 295                 300 gct ttc cgc atc cgc ttt gtt gca cac gct ttc acg ttt gct atc gct    960
Ala Phe Arg Ile Arg Phe Val Ala His Ala Phe Thr Phe Ala Ile Ala
305                 310                 315                 320 ctg cac aaa gcc gct gca gct ttt acg gca gcc ttt ttt ggt ttt ttt   1008
Leu His Lys Ala Ala Ala Ala Phe Thr Ala Ala Phe Phe Gly Phe Phe
                325                 330                 335 aat cgg aat gcc ttt cag aat ggt cac ttt gcc ttt cgg ttt acg cac   1056
Asn Arg Asn Ala Phe Gln Asn Gly His Phe Ala Phe Arg Phe Thr His
            340                 345                 350 ttt acg aaa gtt cac atc atc cac gcc ttc atc ttc ttt cag cag cag   1104
Phe Thr Lys Val His Ile Ile His Ala Phe Ile Phe Phe Gln Gln Gln
        355                 360                 365 atg ggt gct ggt aaa gtt gct cag gcc acg gct ttc ctg cag ttc gct   1152
Met Gly Ala Gly Lys Val Ala Gln Ala Thr Ala Phe Leu Gln Phe Ala
370                 375                 380 gct gct gct cgg cgg cat aaa cac atc ttt ttt gca ttt gct acg ggt   1200
Ala Ala Ala Arg Arg His Lys His Ile Phe Phe Ala Phe Ala Thr Gly
385                 390                 395                 400 acg cag gtt cca gtt gct gtt gtt gct ctg gtt ctg cag atg gct ggt   1248
Thr Gln Val Pro Val Ala Val Val Ala Leu Val Leu Gln Met Ala Gly
                405                 410                 415 cag cgc cgc cat gct gca atc ttt ata acg gct ttt aat gcc acg ttt   1296
Gln Arg Arg His Ala Ala Ile Phe Ile Thr Ala Phe Asn Ala Thr Phe
            420                 425                 430 gct cag cac ggt aaa atc aaa atc ttc cgg ttt cag gct ggt ttc gcc   1344
Ala Gln His Gly Lys Ile Lys Ile Phe Arg Phe Gln Ala Gly Phe Ala
        435                 440                 445 gtt ttt atg cag ata gtt cgc cag gct gct ttt gct acg aaa ttt cag   1392
Val Phe Met Gln Ile Val Arg Gln Ala Ala Phe Ala Thr Lys Phe Gln
450                 455                 460 gcc ctg cgg gct aat aaa ata cac atc aaa acg gcc cgc ggt ttt gcc   1440
Ala Leu Arg Ala Asn Lys Ile His Ile Lys Thr Ala Arg Gly Phe Ala
465                 470                 475                 480 aaa cag acg ctg ttt cac cac acg ttc cca gcc gca cgg cac gct ttt   1488
Lys Gln Thr Leu Phe His His Thr Phe Pro Ala Ala Arg His Ala Phe
                485                 490                 495 acg gca ttc ggt gcc cgc ggt cgc gcc aaa ctg cgc gct cgc aat cgg   1536
```

```
Thr Ala Phe Gly Ala Arg Gly Arg Ala Lys Leu Arg Ala Arg Asn Arg
                500                 505                 510 ttc ctg cag cag cgg gtt gca ttc gct gct acg ttt aat cat cat ctg      1584
Phe Leu Gln Gln Arg Val Ala Phe Ala Ala Thr Phe Asn His His Leu
            515                 520                 525 ttc ttc atc ttc gcc cac acg ttc cag ttc cat cgc cac atc ttc ttt      1632
Phe Phe Ile Phe Ala His Thr Phe Gln Phe His Arg His Ile Phe Phe
    530                 535                 540 acg cag atc gtt cgg cgg atc cgg cac cag acg ttc gct gct ggt cac      1680
Thr Gln Ile Val Arg Arg Ile Arg His Gln Thr Phe Ala Ala Gly His
545                 550                 555                 560 ggt cgg cgc cgc gcc acg atc gcc cag gct cag gct ttc cag gcc ggt      1728
Gly Arg Arg Arg Ala Thr Ile Ala Gln Ala Gln Ala Phe Gln Ala Gly
                565                 570                 575 ggt gcc cat ggt cgc cag ttt ggt acc                                  1755
Gly Ala His Gly Arg Gln Phe Gly Thr
            580                 585

<210> SEQ ID NO 10
<211> LENGTH: 585
<212> TYPE: PRT
<213> ORGANISM: Homo sapiens

<400> SEQUENCE: 10

Glu Leu Gln Leu Leu Ala Gln Ala Gln Phe Phe Met Val Phe Pro Gln
1               5                   10                  15

Pro Ile Met Ile Phe Val Gln Phe Met Ile Phe Arg Met His Leu Phe
                20                  25                  30

Pro Phe Val His Ala Lys Asn Thr Ile Ala Ile Val Ala Ile Phe Ala
            35                  40                  45

Asn Ala Met Gln Phe Asn Arg Ile Phe Pro Leu Phe Gly Gln Ile Phe
    50                  55                  60

Ile Ala Lys Phe His Asn Gly Phe Arg Thr Gln Ile Ile Gln Ala Gln
65                  70                  75                  80

Arg Phe Gln Gln Phe Ala His Ile Thr Pro Ile Arg Gly Thr Arg His
                85                  90                  95

Phe Arg Ala Arg Ile Phe Phe Gln Lys Phe Pro Gln His Arg Asn Arg
            100                 105                 110

His Phe Ala Ala Gly Thr Val Gln Lys Asn Gly Arg Asn Gln Gln Phe
    115                 120                 125

Pro Arg Ile Met Lys Gln Gly Phe Leu His Gln Val Lys Arg Ala Thr
130                 135                 140

Arg Arg Gly Pro Phe Phe Lys Arg Phe Thr Thr Arg Arg Ala Gln Arg
145                 150                 155                 160

Phe Phe Val Ile Phe Ala Ala Lys Ile Gln Ala Gly Phe Thr Thr Phe
                165                 170                 175

Asn Leu Gly Thr Arg Asn Gly Ile Phe Gly Lys Ile Phe Thr Gly Arg
            180                 185                 190

Ala Ala Val Val Ile His Phe Ala Ala Thr Phe Gln Asn Ile Gly Met
    195                 200                 205

Gln Met Phe Phe Thr Phe His His Phe His Gly Ala Asn Phe Phe
210                 215                 220

Ala Phe Gln Lys Gly Ile Phe Ile Phe Val Met Phe Ala Ile Phe
225                 230                 235                 240

Arg Ala Ala Lys Phe Val Asn Asn Ala Ala Gly Phe Leu Phe Ala Ala
                245                 250                 255
```

```
Lys Val Ala Ala Ala Gln Ala Thr Phe Phe Phe His Gln Ala
            260                 265                 270

Val Phe Phe Ala Gly His Ala Gln Gly Phe Ala Ala Arg Ala Arg Ile
        275                 280                 285

Ala Asn Ala His Gly Thr Ile Gln Leu Ala Phe Leu Arg His Arg Phe
    290                 295                 300

Ala Phe Arg Ile Arg Phe Val Ala His Ala Phe Thr Phe Ala Ile Ala
305                 310                 315                 320

Leu His Lys Ala Ala Ala Phe Thr Ala Phe Phe Gly Phe Phe
                325                 330                 335

Asn Arg Asn Ala Phe Gln Asn Gly His Phe Ala Phe Arg Phe Thr His
                340                 345                 350

Phe Thr Lys Val His Ile Ile His Ala Phe Ile Phe Gln Gln Gln
            355                 360                 365

Met Gly Ala Gly Lys Val Ala Gln Ala Thr Ala Phe Leu Gln Phe Ala
        370                 375                 380

Ala Ala Ala Arg Arg His Lys His Ile Phe Phe Ala Phe Ala Thr Gly
385                 390                 395                 400

Thr Gln Val Pro Val Ala Val Val Ala Leu Val Leu Gln Met Ala Gly
            405                 410                 415

Gln Arg Arg His Ala Ala Ile Phe Ile Thr Ala Phe Asn Ala Thr Phe
        420                 425                 430

Ala Gln His Gly Lys Ile Lys Ile Phe Arg Phe Gln Ala Gly Phe Ala
    435                 440                 445

Val Phe Met Gln Ile Val Arg Gln Ala Ala Phe Ala Thr Lys Phe Gln
        450                 455                 460

Ala Leu Arg Ala Asn Lys Ile His Ile Lys Thr Ala Arg Gly Phe Ala
465                 470                 475                 480

Lys Gln Thr Leu Phe His His Thr Phe Pro Ala Ala Arg His Ala Phe
                485                 490                 495

Thr Ala Phe Gly Ala Arg Gly Arg Ala Lys Leu Arg Ala Arg Asn Arg
            500                 505                 510

Phe Leu Gln Gln Arg Val Ala Phe Ala Ala Thr Phe Asn His His Leu
        515                 520                 525

Phe Phe Ile Phe Ala His Thr Phe Gln Phe His Arg His Ile Phe Phe
    530                 535                 540

Thr Gln Ile Val Arg Arg Ile Arg His Gln Thr Phe Ala Ala Gly His
545                 550                 555                 560

Gly Arg Arg Arg Ala Thr Ile Gln Ala Gln Ala Phe Gln Ala Gly
                565                 570                 575

Gly Ala His Gly Arg Gln Phe Gly Thr
            580                 585

<210> SEQ ID NO 11
<211> LENGTH: 1755
<212> TYPE: DNA
<213> ORGANISM: Homo sapiens
<220> FEATURE:
<221> NAME/KEY: CDS
<222> LOCATION: (1)..(1740)

<400> SEQUENCE: 11 ggt acc aaa ctg gcg acc atg ggc acc acc ggc ctg gaa agc ctg agc      48
Gly Thr Lys Leu Ala Thr Met Gly Thr Thr Gly Leu Glu Ser Leu Ser
1               5                   10                  15 ctg ggc gat cgt ggc gcg gcg ccg acc gtg acc agc agc gaa cgt ctg      96
```

```
                Leu Gly Asp Arg Gly Ala Ala Pro Thr Val Thr Ser Ser Glu Arg Leu
                            20                  25                  30 gtg ccg gat ccg ccg aac gat ctg cgt aaa gaa gat gtg gcg atg gaa          144
Val Pro Asp Pro Pro Asn Asp Leu Arg Lys Glu Asp Val Ala Met Glu
         35                  40                  45 ctg gaa cgt gtg ggc gaa gat gaa gaa cag atg atg att aaa cgt agc          192
Leu Glu Arg Val Gly Glu Asp Glu Glu Gln Met Met Ile Lys Arg Ser
 50                  55                  60 agc gaa tgc aac ccg ctg ctg cag gaa ccg att gcg agc gcg cag ttt          240
Ser Glu Cys Asn Pro Leu Leu Gln Glu Pro Ile Ala Ser Ala Gln Phe
 65                  70                  75                  80 ggc gcg acc gcg ggc acc gaa tgc cgt aaa agc gtg ccg tgc ggc tgg          288
Gly Ala Thr Ala Gly Thr Glu Cys Arg Lys Ser Val Pro Cys Gly Trp
             85                  90                  95 gaa cgt gtg gtg aaa cag cgt ctg ttt ggc aaa acc gcg ggc cgt ttt          336
Glu Arg Val Val Lys Gln Arg Leu Phe Gly Lys Thr Ala Gly Arg Phe
                100                 105                 110 gat gtg tat ttt att agc ccg cag ggc ctg aaa ttt cgt agc aaa agc          384
Asp Val Tyr Phe Ile Ser Pro Gln Gly Leu Lys Phe Arg Ser Lys Ser
            115                 120                 125 agc ctg gcg aac tat ctg cat aaa aac ggc gaa acc agc ctg aaa ccg          432
Ser Leu Ala Asn Tyr Leu His Lys Asn Gly Glu Thr Ser Leu Lys Pro
        130                 135                 140 gaa gat ttt gat ttt acc gtg ctg agc aaa cgt ggc att aaa agc cgt          480
Glu Asp Phe Asp Phe Thr Val Leu Ser Lys Arg Gly Ile Lys Ser Arg
145                 150                 155                 160 tat aaa gat tgc agc atg gcg gcg ctg acc agc cat ctg cag aac cag          528
Tyr Lys Asp Cys Ser Met Ala Ala Leu Thr Ser His Leu Gln Asn Gln
                165                 170                 175 agc aac aac agc aac tgg aac ctg cgt acc cgt agc aaa tgc aaa aaa          576
Ser Asn Asn Ser Asn Trp Asn Leu Arg Thr Arg Ser Lys Cys Lys Lys
            180                 185                 190 gat gtg ttt atg ccg ccg agc agc agc gaa ctg cag gaa agc cgt          624
Asp Val Phe Met Pro Pro Ser Ser Ser Glu Leu Gln Glu Ser Arg
        195                 200                 205 ggc ctg agc aac ttt acc agc acc cat ctg ctg ctg aaa gaa gat gaa          672
Gly Leu Ser Asn Phe Thr Ser Thr His Leu Leu Leu Lys Glu Asp Glu
    210                 215                 220 ggc gtg gat gat gtg aac ttt cgt aaa gtg cgt aaa ccg aaa ggc aaa          720
Gly Val Asp Asp Val Asn Phe Arg Lys Val Arg Lys Pro Lys Gly Lys
225                 230                 235                 240 gtg acc att ctg aaa ggc att ccg att aaa aaa acc aaa aaa ggc tgc          768
Val Thr Ile Leu Lys Gly Ile Pro Ile Lys Lys Thr Lys Lys Gly Cys
                245                 250                 255 cgt aaa agc tgc agc ggc ttt gtg cag agc gat agc aaa cgt gaa agc          816
Arg Lys Ser Cys Ser Gly Phe Val Gln Ser Asp Ser Lys Arg Glu Ser
            260                 265                 270 gtg tgc aac aaa gcg gat gcg gaa agc gaa ccg gtg gcg cag aaa agc          864
Val Cys Asn Lys Ala Asp Ala Glu Ser Glu Pro Val Ala Gln Lys Ser
        275                 280                 285 cag ctg gat cgt acc gtg tgc att agc gat gcg ggc gcg tgc ggc gaa          912
Gln Leu Asp Arg Thr Val Cys Ile Ser Asp Ala Gly Ala Cys Gly Glu
    290                 295                 300 acc ctg agc gtg acc agc gaa gaa aac agc ctg gtg aaa aaa aaa gaa          960
Thr Leu Ser Val Thr Ser Glu Glu Asn Ser Leu Val Lys Lys Lys Glu
305                 310                 315                 320 cgt agc ctg agc agc ggc agc aac ttt tgc agc gaa cag aaa acc agc          1008
Arg Ser Leu Ser Ser Gly Ser Asn Phe Cys Ser Glu Gln Lys Thr Ser
                325                 330                 335
```

```
ggc att att aac aaa ttt tgc agc gcg aaa gat agc gaa cat aac gaa    1056
Gly Ile Ile Asn Lys Phe Cys Ser Ala Lys Asp Ser Glu His Asn Glu
            340                 345                 350 aaa tat gaa gat acc ttt ctg gaa agc gaa gaa att ggc acc aaa gtg    1104
Lys Tyr Glu Asp Thr Phe Leu Glu Ser Glu Glu Ile Gly Thr Lys Val
        355                 360                 365 gaa gtg gtg gaa cgt aaa gaa cat ctg cat acc gat att ctg aaa cgt    1152
Glu Val Val Glu Arg Lys Glu His Leu His Thr Asp Ile Leu Lys Arg
    370                 375                 380 ggc agc gaa atg gat aac aac tgc agc ccg acc cgt aaa gat ttt acc    1200
Gly Ser Glu Met Asp Asn Asn Cys Ser Pro Thr Arg Lys Asp Phe Thr
385                 390                 395                 400 gaa gat acc att ccg cgt acc cag att gaa cgt cgt aaa acc agc ctg    1248
Glu Asp Thr Ile Pro Arg Thr Gln Ile Glu Arg Arg Lys Thr Ser Leu
                405                 410                 415 tat ttt agc agc aaa tat aac aaa gaa gcg ctg agc ccg ccg cgt cgt    1296
Tyr Phe Ser Ser Lys Tyr Asn Lys Glu Ala Leu Ser Pro Pro Arg Arg
            420                 425                 430 aaa gcg ttt aaa aaa tgg acc ccg ccg cgt agc ccg ttt aac ctg gtg    1344
Lys Ala Phe Lys Lys Trp Thr Pro Pro Arg Ser Pro Phe Asn Leu Val
        435                 440                 445 cag gaa acc ctg ttt cat gat ccg tgg aaa ctg ctg att gcg acc att    1392
Gln Glu Thr Leu Phe His Asp Pro Trp Lys Leu Leu Ile Ala Thr Ile
    450                 455                 460 ttt ctg aac cgt acc agc ggc aaa atg gcg att ccg gtg ctg tgg aaa    1440
Phe Leu Asn Arg Thr Ser Gly Lys Met Ala Ile Pro Val Leu Trp Lys
465                 470                 475                 480 ttt ctg gaa aaa tat ccg agc gcg gaa gtg gcg cgt acc gcg gat tgg    1488
Phe Leu Glu Lys Tyr Pro Ser Ala Glu Val Ala Arg Thr Ala Asp Trp
                485                 490                 495 cgt gat gtg agc gaa ctg ctg aaa ccg ctg ggc ctg tat gat ctg cgt    1536
Arg Asp Val Ser Glu Leu Leu Lys Pro Leu Gly Leu Tyr Asp Leu Arg
            500                 505                 510 gcg aaa acc att gtg aaa ttt agc gat gaa tat ctg acc aaa cag tgg    1584
Ala Lys Thr Ile Val Lys Phe Ser Asp Glu Tyr Leu Thr Lys Gln Trp
        515                 520                 525 aaa tat ccg att gaa ctg cat ggc att ggc aaa tat ggc aac gat agc    1632
Lys Tyr Pro Ile Glu Leu His Gly Ile Gly Lys Tyr Gly Asn Asp Ser
    530                 535                 540 tat cgt att ttt tgc gtg aac gaa tgg aaa cag gtg cat ccg gaa gat    1680
Tyr Arg Ile Phe Cys Val Asn Glu Trp Lys Gln Val His Pro Glu Asp
545                 550                 555                 560 cat aaa ctg aac aaa tat cat gat tgg ctg tgg gaa aac cat gaa aaa    1728
His Lys Leu Asn Lys Tyr His Asp Trp Leu Trp Glu Asn His Glu Lys
                565                 570                 575 ctg agc ctg agc taataactgg agctc                                    1755
Leu Ser Leu Ser
            580

<210> SEQ ID NO 12
<211> LENGTH: 580
<212> TYPE: PRT
<213> ORGANISM: Homo sapiens

<400> SEQUENCE: 12

Gly Thr Lys Leu Ala Thr Met Gly Thr Thr Gly Leu Glu Ser Leu Ser
1               5                   10                  15

Leu Gly Asp Arg Gly Ala Ala Pro Thr Val Thr Ser Ser Glu Arg Leu
            20                  25                  30

Val Pro Asp Pro Pro Asn Asp Leu Arg Lys Glu Asp Val Ala Met Glu
```

```
            35                  40                  45
Leu Glu Arg Val Gly Glu Asp Glu Gln Met Met Ile Lys Arg Ser
 50                  55                  60

Ser Glu Cys Asn Pro Leu Leu Gln Glu Pro Ile Ala Ser Ala Gln Phe
 65                  70                  75                  80

Gly Ala Thr Ala Gly Thr Glu Cys Arg Lys Ser Val Pro Cys Gly Trp
                 85                  90                  95

Glu Arg Val Val Lys Gln Arg Leu Phe Gly Lys Thr Ala Gly Arg Phe
                100                 105                 110

Asp Val Tyr Phe Ile Ser Pro Gln Gly Leu Lys Phe Arg Ser Lys Ser
            115                 120                 125

Ser Leu Ala Asn Tyr Leu His Lys Asn Gly Glu Thr Ser Leu Lys Pro
130                 135                 140

Glu Asp Phe Asp Phe Thr Val Leu Ser Lys Arg Gly Ile Lys Ser Arg
145                 150                 155                 160

Tyr Lys Asp Cys Ser Met Ala Ala Leu Thr Ser His Leu Gln Asn Gln
                165                 170                 175

Ser Asn Asn Ser Asn Trp Asn Leu Arg Thr Arg Ser Lys Cys Lys Lys
            180                 185                 190

Asp Val Phe Met Pro Pro Ser Ser Ser Glu Leu Gln Glu Ser Arg
            195                 200                 205

Gly Leu Ser Asn Phe Thr Ser Thr His Leu Leu Leu Lys Glu Asp Glu
210                 215                 220

Gly Val Asp Asp Val Asn Phe Arg Lys Val Arg Lys Pro Lys Gly Lys
225                 230                 235                 240

Val Thr Ile Leu Lys Gly Ile Pro Ile Lys Lys Thr Lys Lys Gly Cys
                245                 250                 255

Arg Lys Ser Cys Ser Gly Phe Val Gln Ser Asp Ser Lys Arg Glu Ser
            260                 265                 270

Val Cys Asn Lys Ala Asp Ala Glu Ser Glu Pro Val Ala Gln Lys Ser
            275                 280                 285

Gln Leu Asp Arg Thr Val Cys Ile Ser Asp Ala Gly Ala Cys Gly Glu
            290                 295                 300

Thr Leu Ser Val Thr Ser Glu Glu Asn Ser Leu Val Lys Lys Lys Glu
305                 310                 315                 320

Arg Ser Leu Ser Ser Gly Ser Asn Phe Cys Ser Glu Gln Lys Thr Ser
                325                 330                 335

Gly Ile Ile Asn Lys Phe Cys Ser Ala Lys Asp Ser Glu His Asn Glu
                340                 345                 350

Lys Tyr Glu Asp Thr Phe Leu Glu Ser Glu Ile Gly Thr Lys Val
            355                 360                 365

Glu Val Val Glu Arg Lys Glu His Leu His Thr Asp Ile Leu Lys Arg
            370                 375                 380

Gly Ser Glu Met Asp Asn Asn Cys Ser Pro Thr Arg Lys Asp Phe Thr
385                 390                 395                 400

Glu Asp Thr Ile Pro Arg Thr Gln Ile Glu Arg Arg Lys Thr Ser Leu
                405                 410                 415

Tyr Phe Ser Ser Lys Tyr Asn Lys Glu Ala Leu Ser Pro Pro Arg Arg
            420                 425                 430

Lys Ala Phe Lys Lys Trp Thr Pro Pro Arg Ser Pro Phe Asn Leu Val
            435                 440                 445

Gln Glu Thr Leu Phe His Asp Pro Trp Lys Leu Leu Ile Ala Thr Ile
450                 455                 460
```

```
Phe Leu Asn Arg Thr Ser Gly Lys Met Ala Ile Pro Val Leu Trp Lys
465                 470                 475                 480

Phe Leu Glu Lys Tyr Pro Ser Ala Glu Val Ala Arg Thr Ala Asp Trp
                485                 490                 495

Arg Asp Val Ser Glu Leu Leu Lys Pro Leu Gly Leu Tyr Asp Leu Arg
            500                 505                 510

Ala Lys Thr Ile Val Lys Phe Ser Asp Glu Tyr Leu Thr Lys Gln Trp
        515                 520                 525

Lys Tyr Pro Ile Glu Leu His Gly Ile Gly Lys Tyr Gly Asn Asp Ser
    530                 535                 540

Tyr Arg Ile Phe Cys Val Asn Glu Trp Lys Gln Val His Pro Glu Asp
545                 550                 555                 560

His Lys Leu Asn Lys Tyr His Asp Trp Leu Trp Glu Asn His Glu Lys
                565                 570                 575

Leu Ser Leu Ser
            580

<210> SEQ ID NO 13
<211> LENGTH: 1360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (28)..(489)
<220> FEATURE:
<221> NAME/KEY: CDS
<222> LOCATION: (493)..(1305)
<220> FEATURE:
<221> NAME/KEY: CDS
<222> LOCATION: (1309)..(1329)
<220> FEATURE:
<221> NAME/KEY: CDS
<222> LOCATION: (1333)..(1356)

<400> SEQUENCE: 13
cattgcacaa gataaaaata tatcatc atg gaa aca gct atg acc atg agc ggt      54
                        Met Glu Thr Ala Met Thr Met Ser Gly
                        1               5 gaa aat gaa gcc aga acc ctg att agc tct att ctg ggc aaa att aaa      102
Glu Asn Glu Ala Arg Thr Leu Ile Ser Ser Ile Leu Gly Lys Ile Lys
 10              15                  20                  25 ggc ctg gtg cag cca acc aga ctg caa tta acc ctc act aaa ggg gag      150
Gly Leu Val Gln Pro Thr Arg Leu Gln Leu Thr Leu Thr Lys Gly Glu
             30                  35                  40 ctc gag gcc cag ccg gcc ggc ctg cag ggc gcg ccg gat ccc ggg gat      198
Leu Glu Ala Gln Pro Ala Gly Leu Gln Gly Ala Pro Asp Pro Gly Asp
         45                  50                  55 atc cat atg gaa ttc gtc gac aag ctt cta gat ctg gct agc acc ggt      246
Ile His Met Glu Phe Val Asp Lys Leu Leu Asp Leu Ala Ser Thr Gly
     60                  65                  70 acc gcg gcc gcg agc cct ata gtg agt cgt att agc ggt ggc gat cat      294
Thr Ala Ala Ala Ser Pro Ile Val Ser Arg Ile Ser Gly Gly Asp His
 75                  80                  85 ccg ccg aaa agc gat ctg gtg ccg cgt ggt agc ccg gaa ttt ccg ggc      342
Pro Pro Lys Ser Asp Leu Val Pro Arg Gly Ser Pro Glu Phe Pro Gly
             90                  95                 100                 105 cgt ctg gaa cgt gac gca aat ata gag ctt gca tgt cta gcc gta gac      390
Arg Leu Glu Arg Asp Ala Asn Ile Glu Leu Ala Cys Leu Ala Val Asp
                110                 115                 120
```

```
att gca ctg gcc gtc gtt tta cag cta atc gtt aat cta ata gct aat    438
Ile Ala Leu Ala Val Val Leu Gln Leu Ile Val Asn Leu Ile Ala Asn
            125                 130                 135 agc gaa ggc ggt ggt agc gaa ggt ggt ggc agt gag ggt ggc ggt tct    486
Ser Glu Gly Gly Gly Ser Glu Gly Gly Gly Ser Glu Gly Gly Gly Ser
            140                 145                 150 gaa taa atg atc ata agc cat att caa cgg gaa acg tcg agg ccg cga    534
Glu     Met Ile Ile Ser His Ile Gln Arg Glu Thr Ser Arg Pro Arg
                155                 160                 165 tta aat tcc aac atg gat gct gat tta tat ggg tat aaa tgg gct cgc    582
Leu Asn Ser Asn Met Asp Ala Asp Leu Tyr Gly Tyr Lys Trp Ala Arg
        170                 175                 180 gat aat gtc ggg caa tca ggt gcg aca atc tat cgc ttg tat ggg aag    630
Asp Asn Val Gly Gln Ser Gly Ala Thr Ile Tyr Arg Leu Tyr Gly Lys
185                 190                 195                 200 ccc gat gcg cca gag ttg ttt ctg aaa cat ggc aaa ggt agc gtt gcc    678
Pro Asp Ala Pro Glu Leu Phe Leu Lys His Gly Lys Gly Ser Val Ala
                205                 210                 215 aat gat gtt aca gat gag atg gtc aga cta aac tgg ctg acg gaa ttt    726
Asn Asp Val Thr Asp Glu Met Val Arg Leu Asn Trp Leu Thr Glu Phe
        220                 225                 230 atg cct ctt ccg acc atc aag cat ttt atc cgt act cct gat gat gca    774
Met Pro Leu Pro Thr Ile Lys His Phe Ile Arg Thr Pro Asp Asp Ala
        235                 240                 245 tgg tta ctc acc act gcg atc ccc gga aaa aca gca ttc cag gta tta    822
Trp Leu Leu Thr Thr Ala Ile Pro Gly Lys Thr Ala Phe Gln Val Leu
        250                 255                 260 gaa gaa tat cct gat tca ggt gaa aat att gtt gat gcg ctg gca gtg    870
Glu Glu Tyr Pro Asp Ser Gly Glu Asn Ile Val Asp Ala Leu Ala Val
265                 270                 275                 280 ttc ctg cgc cgg ttg cat tcg att cct gtt tgt aat tgt cct ttt aac    918
Phe Leu Arg Arg Leu His Ser Ile Pro Val Cys Asn Cys Pro Phe Asn
                285                 290                 295 agc gat cgc gta ttt cgt ctc gct cag gcg caa tca cga atg aat aac    966
Ser Asp Arg Val Phe Arg Leu Ala Gln Ala Gln Ser Arg Met Asn Asn
        300                 305                 310 ggt ttg gtt gat gcg agt gat ttt gat gac gag cgt aat ggc tgg cct   1014
Gly Leu Val Asp Ala Ser Asp Phe Asp Asp Glu Arg Asn Gly Trp Pro
        315                 320                 325 gtt gaa caa gtc tgg aaa gaa atg cat aaa ctt ttg cca ttc tca ccg   1062
Val Glu Gln Val Trp Lys Glu Met His Lys Leu Leu Pro Phe Ser Pro
330                 335                 340 gat tca gtc gtc act cat ggt gat ttc tca ctt gat aac ctt att ttt   1110
Asp Ser Val Val Thr His Gly Asp Phe Ser Leu Asp Asn Leu Ile Phe
345                 350                 355                 360 gac gag ggg aaa tta ata ggt tgt att gat gtt gga cga gtc gga atc   1158
Asp Glu Gly Lys Leu Ile Gly Cys Ile Asp Val Gly Arg Val Gly Ile
                365                 370                 375 gca gac cga tac cag gat ctt gcc atc cta tgg aac tgc ctc ggt gag   1206
Ala Asp Arg Tyr Gln Asp Leu Ala Ile Leu Trp Asn Cys Leu Gly Glu
        380                 385                 390 ttt tct cct tca tta cag aaa cgg ctt ttt caa aaa tat ggt att gat   1254
Phe Ser Pro Ser Leu Gln Lys Arg Leu Phe Gln Lys Tyr Gly Ile Asp
        395                 400                 405 aat cct gat atg aat aaa ttg cag ttt cat ttg atg ctc gat gag ttt   1302
Asn Pro Asp Met Asn Lys Leu Gln Phe His Leu Met Leu Asp Glu Phe
410                 415                 420 ttc taa tca gaa ttg gtt aat tgg ttg taa cac tgg cag agc att acg   1350
Phe     Ser Glu Leu Val Asn Trp Leu     His Trp Gln Ser Ile Thr
```

```
                425                 430                 435
ctg act tgac                                                              1360
Leu Thr
    440

<210> SEQ ID NO 14
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Glu Thr Ala Met Thr Met Ser Gly Glu Asn Glu Ala Arg Thr Leu
1               5                   10                  15

Ile Ser Ser Ile Leu Gly Lys Ile Lys Gly Leu Val Gln Pro Thr Arg
            20                  25                  30

Leu Gln Leu Thr Leu Thr Lys Gly Glu Leu Glu Ala Gln Pro Ala Gly
        35                  40                  45

Leu Gln Gly Ala Pro Asp Pro Gly Asp Ile His Met Glu Phe Val Asp
    50                  55                  60

Lys Leu Leu Asp Leu Ala Ser Thr Gly Thr Ala Ala Ser Pro Ile
65                  70                  75                  80

Val Ser Arg Ile Ser Gly Gly Asp His Pro Pro Lys Ser Asp Leu Val
                85                  90                  95

Pro Arg Gly Ser Pro Glu Phe Pro Gly Arg Leu Glu Arg Asp Ala Asn
            100                 105                 110

Ile Glu Leu Ala Cys Leu Ala Val Asp Ile Ala Leu Ala Val Val Leu
        115                 120                 125

Gln Leu Ile Val Asn Leu Ile Ala Asn Ser Glu Gly Gly Gly Ser Glu
    130                 135                 140

Gly Gly Gly Ser Glu Gly Gly Gly Ser Glu
145                 150

<210> SEQ ID NO 15
<211> LENGTH: 1360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gtcaagtcag cgtaatgctc tgccagtgtt acaaccaatt aaccaattct gattagaaaa        60
actcatcgag catcaaatga aactgcaatt tattcatatc aggattatca ataccatatt       120
tttgaaaaag ccgtttctgt aatgaaggag aaaactcacc gaggcagttc cataggatgg       180
caagatcctg gtatcggtct gcgattccga ctcgtccaac atcaatacaa cctattaatt       240
tcccctcgtc aaaataagg ttatcaagtg agaaatcacc atgagtgacg actgaatccg        300
gtgagaatgg caaaagttta tgcatttctt tccagacttg ttcaacaggc cagccattac       360
gctcgtcatc aaaatcactc gcatcaacca accgttatt cattcgtgat tgcgcctgag       420
cgagacgaaa tacgcgatcg ctgttaaaag gacaattaca acaggaatc gaatgcaacc       480 ggcgcaggaa cactgccagc gcatcaacaa tattttcacc tgaatcagga tattcttcta       540
atacctggaa tgctgttttt ccggggatcg cagtggtgag taaccatgca tcatcaggag       600
tacggataaa atgcttgatg gtcggaagag gcataaattc cgtcagccag tttagtctga       660
```

```
ccatctcatc tgtaacatca ttggcaacgc tacctttgcc atgtttcaga aacaactctg    720
gcgcatcggg cttcccatac aagcgataga ttgtcgcacc tgattgcccg acattatcgc    780
gagcccattt atacccatat aaatcagcat ccatgttgga atttaatcgc ggcctcgacg    840
tttcccgttg aatatggctt atgatcattt attcagaacc gccaccctca ctgccaccac    900
cttcgctacc accgccttcg ctattagcta ttagattaac gattagctgt aaaacgacgg    960
ccagtgcaat gtctacggct agacatgcaa gctctatatt tgcgtcacgt tccagacggg   1020
ccggaaattc cgggctacca cgcggcacca gatcgctttt cggcggatga tcgccaccgc   1080
taatacgact cactataggg ctcgcggccg cggtaccggt gctagccaga tctagaagct   1140
tgtcgacgaa ttccatatgg atatccccgg gatccggcgc gccctgcagg ccggccggct   1200
gggcctcgag ctccccttta gtgagggtta attgcagtct ggttggctgc accaggcctt   1260
taattttgcc cagaatagag ctaatcaggg ttctggcttc attttcaccg ctcatggtca   1320
tagctgtttc catgatgata tatttttatc ttgtgcaatg                         1360

<210> SEQ ID NO 16
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2)..(112)

<400> SEQUENCE: 16 g gag ctc gag gcc cag ccg gcc ggc ctg cag ggc gcg ccg gat ccc ggg     49
  Glu Leu Glu Ala Gln Pro Ala Gly Leu Gln Gly Ala Pro Asp Pro Gly
  1               5                   10                  15 gat atc cat atg gaa ttc gtc gac aag ctt cta gat ctg gct agc acc      97
Asp Ile His Met Glu Phe Val Asp Lys Leu Leu Asp Leu Ala Ser Thr
            20                  25                  30 ggt acc gcg gcc gcg                                                  112
Gly Thr Ala Ala Ala
        35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Leu Glu Ala Gln Pro Ala Gly Leu Gln Gly Ala Pro Asp Pro Gly
1               5                   10                  15

Asp Ile His Met Glu Phe Val Asp Lys Leu Leu Asp Leu Ala Ser Thr
            20                  25                  30

Gly Thr Ala Ala Ala
        35

<210> SEQ ID NO 18
<211> LENGTH: 6
<212> TYPE: PRT
<213> ORGANISM: Influenza virus

<400> SEQUENCE: 18
```

Gly Ser Ser Arg Glu Leu
1               5

<210> SEQ ID NO 19
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ile Ile Ser His Ile Gln Arg Glu Thr Ser Arg Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Glu Leu Val Asn Trp Leu
1               5

```
<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Trp Gln Ser Ile Thr Leu Thr
1               5
```

METHOD FOR DETERMINING FRAMESHIFT MUTATIONS IN CODING NUCLEIC ACIDS

SEQUENCE LISTING

The instant application contains a Sequence Listing which has been submitted via. EFS-Web and is hereby incorporated by reference in its entirety. Said ASCII copy, created on Jul. 28, 2010, is named WEICKM86.txt, and is 76,815 bytes in size.

The present invention relates to a method for identifying frameshift mutations in coding nucleic acid sequences.

Genetic information is organised in coding nucleic acids in the form of base triplets or codons. However, errors frequently occur in gene synthesis in the form of various kinds of mutations. The majority of the mutations are single-base deletions and insertions (approx. 90%). In contrast with most substitutions, virtually all insertions and deletions give rise to what are known as frameshifts. If a base is lost from a gene in the course of a mutation (deletion) or if a base is added (insertion), this changes the reading frame of the following base triplets. A frameshift mutation has a substantially greater biological impact than a substitution. From the insertion/deletion onwards, other amino acids are encoded and translation is usually terminated due to out-of-frame stop codons.

As the length of a synthesised gene increases, the probability of a mutation occurring likewise greatly increases. The majority of unwanted mutations occur due to the absence or the insertion of individual bases into oligonucleotides. The probability of a base being substituted during the synthesis of genes or gene libraries amounts to approximately 0.1-0.2% per position, while the probability of an insertion/deletion is 1.0-1.5% per position. For example, Kong et al., Nucleic Acids Res. (2007), 35:e61 observed a deletion rate of 1.48% per position and a substitution rate of 0.3% per position in chip-based gene synthesis. Around half of the substitutions were in turn due to PCR errors.

The reading frameshift which occurs in the event of insertions and deletions may be exploited in order, by means of a reporter vector, to select those nucleic acid fragments which have an intact reading frame. European patent application EP 0 872 560 accordingly discloses a method for identifying frameshift mutations, in which homologous recombination is used to produce a construct which contains a promoter, a gene to be investigated and a reporter gene in the same reading frame as the gene to be investigated. Upon expression of the reading frame, a fusion protein is obtained which contains the reporter gene function. The latter may be detected by means of phenotypic characteristics.

One drawback, however, is that, for the procedure described in EP 0 872 560, the gene to be investigated must not comprise any internal stop codons within the open reading frame (ORF). However, many synthesised genes do comprise such internal stop codons.

In the light of the above problem, the object of the present invention was to provide a method for identifying frameshift mutations which is suitable for any coding nucleic acids and in particular also for nucleic acids which comprise internal stop codons.

According to the invention, said object is achieved by a method for identifying frameshift mutations in coding target nucleic acids which comprises the steps:
(i) providing a host cell comprising a double-stranded nucleic acid, which comprises a coding target nucleic acid and a coding opposite strand nucleic acid complementary thereto, in which the opposite strand nucleic acid is present in operative linkage with a reporter gene in 3'-position;
(ii) effecting expression of the opposite strand nucleic acid; and
(iii) identifying whether expression of the reporter gene occurs in the host cell,
in which expression of the reporter gene indicates that the target nucleic acid does not comprise a frameshift mutation.

According to the invention, the phrase "does not comprise a frameshift mutation" should be taken to mean that the target nucleic acid either comprises absolutely no frameshift mutation or that a plurality of mutations are present in the target nucleic acid, which, viewed in isolation, would result in a reading frameshift, but cancel each other out again. For example, a combination of insertions and deletions may be present in the target nucleic acid which however cancel each other out again, such that the reading frame is not modified and the reporter gene may still be correctly read.

The inventors have found that, instead of the coding target nucleic acid, a coding opposite strand nucleic acid complementary thereto may be used to identify frameshift mutations.

In this connection, the term "coding" should be taken to mean that the opposite strand nucleic acid is such that it enables expression of the 3'-linked reporter gene. However, the opposite strand nucleic acid need not necessarily be defined for this purpose by an open reading frame.

When the method according to the invention is carried out, a host cell is first provided which comprises a double-stranded nucleic acid which contains a coding target nucleic acid and a coding opposite strand nucleic acid complementary thereto. The target nucleic acid preferably comprises a synthetically produced sequence. In the host cell, the opposite strand nucleic acid is in operative linkage with a reporter gene which is located downstream in 3'-position.

If the opposite strand nucleic acid is intact, i.e. comprises no mutations such as in particular insertions or deletions which result in a modification of the reading frame, on expression a fusion polypeptide is obtained which comprises the amino acid sequence coded by the opposite strand nucleic acid and, C-terminally therefrom, the amino acid sequence of the product coded by the reporter gene. If, on the other hand, the opposite strand nucleic acid does comprise a frameshift mutation, i.e. in particular an insertion or deletion which modifies the reading frame, this reading frameshift results in the reporter gene not being located in-frame relative to the coding opposite strand nucleic acid. As a result, the reporter gene is not expressed. The reporter is thus only expressed if the reading frame of the opposite strand is intact.

If the opposite strand nucleic acid does not comprise any frameshift mutations, it may be concluded that the complementary target nucleic acid itself is also intact and does not comprise any frameshift mutations.

The method of the present invention has the advantage that, even if internal stop codons are present in the target nucleic acid, it is possible to identify frameshift mutations by using a reporter gene. When the reading frame in the opposite strand is used, internal stop codons of the target nucleic acid are translated as Leu or Ser. Using a reading frame in the opposite strand furthermore has the advantage that any possible toxicity of the protein coded by the actual target nucleic acid for the host cell is irrelevant, as only the opposite strand is translated.

A coding opposite strand nucleic acid is necessary in order to carry out the method according to the invention. A reading frame in the opposite strand may optionally be obtained by appropriate optimisation of the opposite strand sequence. It may furthermore be preferred for the opposite strand nucleic acid to contain no internal stop codons. The complementary codons to the three stop codons are relatively rare, so a reading frame in the opposite strand generally contains no stop codons. In a preferred embodiment the opposite strand nucleic acid is optionally optimised such that no internal stop codons are present.

In a preferred embodiment according to the invention, the opposite strand nucleic acid in the host cell in 3'-position is in operative linkage with a reporter gene and in 5'-position is in operative linkage with an expression control sequence.

According to the invention, an expression control sequence is a nucleic acid sequence which controls and regulates transcription and translation. The expression control sequence may be constitutively or regulatably active in the host cell. The phrase "in operative linkage" includes a suitable start signal (for example ATG or AUG) before the nucleic acid sequence to be expressed and the retention of the correct reading frame, so enabling expression of the nucleic acid sequence under the control of the expression control sequence and the production of the product coded by the nucleic acid sequence. If a nucleic acid does not contain a suitable start signal, such a start signal may be inserted before the nucleic acid.

In one embodiment, the provision of a host cell in step (i) of the method according to the invention involves the introduction of an expression vector into a host cell, wherein the expression vector comprises the double-stranded nucleic acid which comprises a coding target nucleic acid and a coding opposite strand nucleic acid complementary thereto.

Expression vectors are known to a person skilled in the art in the field of molecular biology and are described, for example, in Sambrook et al., Molecular Cloning, A Laboratory Manual (1989), Cold Spring Harbor Laboratory Press. For example, a plasmid or a viral vector may be used as expression vector.

In one embodiment, the opposite strand nucleic acid may be present in the expression vector in operative linkage with a reporter gene in 3'-position. Alternatively, in another embodiment, the expression vector may be introduced into a host cell together with a reporter vector which comprises the reporter gene. In a further embodiment, the expression vector may also be introduced into a host cell which already contains a reporter gene.

The opposite strand nucleic acid in the expression vector is preferably in operative linkage with an expression control sequence in 5'-position. In a particularly preferred embodiment, the opposite strand nucleic acid in the expression vector is in operative linkage in 3'-position with a reporter gene and in 5'-position with an expression control sequence.

An expression vector according to the invention may be produced in any desired manner, for example by culturing in host cells, preferably in bacterial cells such as for instance *E. coli* cells. The expression vector conveniently contains elements which enable replication and selection in the host cell. Alternatively, an expression vector may also be produced in vitro by amplification in sufficient quantity, for example by polymerase chain reaction (PCR), ligase chain reaction (LCR) or rolling circle amplification.

Prokaryotic or eukaryotic cells or microorganisms may be used as host cells. The host cells may be wild-type variants or mutated or genetically manipulated host cells may be used.

According to the invention, a gene which codes for a detectable gene product may be used as a reporter gene. For example, the reporter gene may comprise an antibiotic resistance gene, preferably kanamycin resistance. In another embodiment, a reporter gene may be used which codes for a fluorescent protein such as for instance GFP. It is furthermore possible to use a reporter gene which codes for an enzyme which catalyses a colorimetrically measurable reaction (for example β-galactosidase). In a further embodiment, the reporter gene may code for a gene product which interacts with a nucleic acid sequence present in the host cell or with a gene product expressed in the host cell, whereby a measurable change in metabolic activity comes about.

The expression vector and optionally reporter vector is/are introduced into the host cell in accordance with methods known in the prior art, for example by (co)transfection, (co)transformation or (co)infection of cells. The method is preferably selected such that the double-stranded nucleic acid is introduced into the host cell in such a way that, in the host cell, the opposite strand sequence is in operative linkage with the reporter gene.

In eukaryotic host cells, transfection or cotransfection may, for example, proceed by calcium phosphate coprecipitation, lipofection, electroporation, particle bombardment, by using bacterial proteins or by viral infection via retroviruses, adenoviruses etc.

In a preferred embodiment of the invention, in step (i) of the method a vector is provided which, in addition to the reporter gene in operative linkage with the opposite strand nucleic acid, comprises at least one selection marker gene. The at least one selection marker gene is selected from any desired genes which code for a detectable gene product, wherein the gene product preferably differs from the gene product of the reporter gene. For example, the selection marker gene may comprise an antibiotic resistance gene such as for instance β-lactamase for ampicillin resistance. Alternatively, a gene which codes for a fluorescent protein such as for instance GP may be used as a selection marker gene.

Selection may proceed independently of the reporter gene by means of the selection marker gene. For example, after selection for the first reporter gene (for example for kanamycin resistance), a construct may be further up-amplified by selection by means of the further selection marker gene (for example for ampicillin resistance). It is furthermore possible to further amplify constructs which contain a frameshift mutation (for example an intentional frameshift mutation) by selection via the second selection marker gene.

Finally, the second selection marker gene may assist in disguising the existence of the reporter gene in connection with a selection which has taken place, in order to protect the method from imitation.

Step (ii) of the method according to the invention involves effecting expression of the opposite strand nucleic acid in the host cell. To this end, the host cell is cultured under suitable conditions which permit expression of the opposite strand nucleic acid.

Step (iii) involves identifying whether expression of the reporter gene occurs in the host cell. The identification is based on the detection of a gene product coded by the reporter vector. Depending on the reporter gene used, the identification may in principle comprise the identification of any phenotypically recognisable effects, for example morphological changes, changes to growth behaviour, etc. If, for example, the reporter gene codes for a fluorescent protein such as GFP, the presence and/or the intensity of luminescence may for example be identified by fluorescence cytometry or imaging assays. If an antibiotic resistance gene is used as reporter gene, the identification may be made on the basis of the growth of host cells in the presence of antibiotics.

In one embodiment of the invention, a target nucleic acid may be assembled from two, three or more subfragments. For example, in the case of a 3 kB construct, three subfragments may first be produced from oligonucleotides and these subfragments then fused to form a 3 kB fragment, for example by fusion PCR. A construct fused in this manner from two or more subfragments may then be ligated directly into an expression vector according to the invention.

Since the method according to the invention is capable of identifying frameshift mutations, but not mutations where the reading frame is maintained, in the event that the target nucleic acid is synthesised by PCR the amplification primer is preferably added at the latest possible time in order to keep the number of amplification steps as small as possible. The greater the number of amplifiable full-length molecules, the fewer the mutations arising due to PCR which will be present in the PCR product.

Ofloxacin, for example, may be used after transformation in order to reduce substitutions still further. Ofloxacin is a gyrase inhibitor which inhibits DNA replication but, over the short term, does not kill host cells such as $E.\ coli$ cells. During this period, a host cell has the opportunity to cleave heterodimers via an internal repair mechanism. Ofloxacin may preferably be present in the medium after electroporation or heat-shock transformation (0.5-1 h at 37° C.). The cells are then centrifuged off, the medium together with the ofloxacin removed and the cells are plated out.

The above-stated method is based on the fact that only in the absence of frameshift mutations does translation of the opposite strand give rise to a fusion protein which comprises the reporter. Under certain circumstances, due to its size, such a fusion protein has an elevated molecular weight and may be present in the cell in the form of denatured aggregates. Even if the correct reading frame is inserted, the expression and functionality of the reporter may thus be affected or even inhibited by the properties of the polypeptide formed. This may lead to a reduction in the efficiency of the method, in particular in the case of relatively large coding target nucleic acids and corresponding opposite strand nucleic acids.

The previously disclosed procedure was further developed by the inventors in the light of this problematic issue. It has surprisingly been found that the strategy of translational coupling known in the field may be used in the above method of operative linkage of the coding opposite strand nucleic acid with a reporter gene in 3'-position.

The phenomenon of conjugated translation or translational coupling is a control mechanism in which the translation of an upstream gene regulates the translation of a downstream gene. One theory to explain this phenomenon assumes that the ribosome from the translated upstream gene is passed on to the downstream gene via a translational coupling signal which acts as a weak ribosome-binding site. The ribosome is not rebound here, but instead, once translation of the upstream gene is complete, the ribosome can scan the sequence and initiate translation of the downstream gene. Translational coupling between two cistrons is thus mediated via the same ribosome. The ribosome terminates translation at a stop codon in the upstream sequence and thereupon scans the downstream sequence, beginning the new translation at a start codon in the vicinity of this stop codon. This scanning operation by the ribosome proceeds in both directions, such that continuation of synthesis may be initiated at a start codon which overlaps with the stop codon of the preceding coding sequence.

Translational coupling was described for the first time by Oppenheim 1980 for the tryptophan operon in $E.\ coli$ (D. S. Oppenheim and C. Yanowski (1980), Genetics 95:789-795). The effect is based on the fact that translation restarts after a stop codon where there is a start codon following directly thereafter. This gives rise to two separate polypeptide chains. A prerequisite for the synthesis of the second polypeptide is that the first reading frame is correctly read up to the stop codon.

WO 2008/077881 describes a method for selecting genes from a gene library for improved expression efficiency, improved expression being quantified by means of a reporter gene which is synthesised by translational coupling with the corresponding gene. Genes with an open reading frame are simultaneously identified by this method. E.g. resistance genes or GFP are mentioned as reporters. It is additionally noted that the start codon of the reporter gene may both overlap with the stop codon of the open reading frame and be at a distance of up to 500 nucleotides.

WO 2008/051619 describes a method for screening DNA libraries for identifying DNA fragments with an open reading frame which comprise neither internal ribosomal binding sites nor internal stop codons. The sequences are selected by using reporter proteins which are not synthesised by covalent fusion with the corresponding reading frame, but instead by translational coupling, in order to prevent misfolding or malfunction of a corresponding fusion protein. The document additionally discloses two vector variants which either enable positive selection of open reading frames without stop codons via resistance markers, or effect negative selection of open reading frames with internal ribosomal binding sites by expression of a toxin.

Ohashi-Kunihiro et al. (Biotechniques (2007) 43(6):741-2, 754) likewise describe the selection of DNA fragments with an open reading frame by translational coupling with a resistance marker which is only expressed in the absence of internal stop codons. Further, the optimal distance between the open reading frame and the resistance marker is determined.

It has now surprisingly been found in the present invention that the strategy of translational coupling may be used in the previously disclosed method for selecting coding nucleic acid constructs for the absence of frameshift mutations. However, in contrast with the method described in the prior art, in the method according to the invention the open reading frame of the opposite strand of the coding target nucleic acid is selected by translational coupling.

The invention therefore provides a method for identifying frameshift mutations in coding target nucleic acids which comprises the steps:
(i) providing a host cell comprising a double-stranded nucleic acid, which comprises a coding target nucleic acid and a coding opposite strand nucleic acid complementary thereto, in which the opposite strand nucleic acid is linked via a linker with a reporter gene in 3'-position;
(ii) effecting expression of the opposite strand nucleic acid; and
(iii) identifying whether expression of the reporter gene occurs in the host cell,
in which expression of the reporter gene indicates that the target nucleic acid does not comprise a frameshift mutation, characterised in that the linker comprises a translational coupler sequence which comprises a stop codon in frame to the reading frame of the opposite strand nucleic acid and a start codon, wherein the reporter gene is located in frame to the start codon.

If the opposite strand nucleic acid (and thus also the complementary target nucleic acid) does not comprise a frameshift mutation, the opposite strand may be correctly read up to the stop codon of the translational coupler sequence in the linker bound in 3'-position. Translation then restarts at the subsequent start codon of the translational coupler sequence. Since the start codon in the linker used according to the invention is in frame to a subsequent reporter gene, the reporter gene is in this case also translated.

By using translational coupling in the method of the present invention, the expression product of the opposite strand nucleic acid to be checked and of the reporter gene are accordingly obtained as separate polypeptide chains.

With the assistance of the method according to the invention, even if internal stop codons are present in a target nucleic acid, frameshift mutations may successfully be identified by means of a reporter gene by using the opposite strand nucleic acid. When the reading frame in the opposite strand is used, internal stop codons of the target nucleic acid are translated as Leu or Ser. Using a reading frame in the opposite strand furthermore has the advantage that any possible toxicity of the protein coded by the actual target nucleic acid for the host cell is irrelevant, as only the opposite strand is translated.

According to the invention, a translational coupler sequence comprises a stop codon, which is arranged in frame to the opposite strand nucleic acid, and a subsequent start codon, which is arranged in frame to the reporter gene. The distance between the stop codon and start codon is selected such that translational coupling is enabled. The distance preferably amounts to no more than 10 base pairs.

In one embodiment of the present invention, the start codon and stop codon of the translational coupler sequence follow on immediately from one another. The translational coupler sequence may, for example, comprise two separate codons, for example TAA ATG. In another embodiment, the start codon and stop codon of the translational coupler sequence overlap with one another. One example of an overlap of the stop codon with the start codon is the translational coupler sequence TAATG.

The coupling of translation at the genetic level according to the invention with simultaneous decoupling of the resultant polypeptide chains results in a significant improvement to the method for identifying correct reading frames. The system remains independent of the folding of the polypeptide chain formed by the opposite strand nucleic acid.

In a preferred embodiment of the invention, the linker contains, in the reading frames shifted by +1 and −1, further stop codons located upstream of the stop codon of the translational coupler sequence. These stop codons ensure that translation of the shifted reading frames is terminated before the stop codon of the translational coupler sequence is reached. The distance of the further stop codons from the start codon of the translational coupler sequence is here preferably selected such that no translational coupling occurs. A distance of at least 30 base pairs, preferably of at least 50 base pairs, has proved to be particularly suitable.

In a preferred embodiment, the opposite strand nucleic acid in the host cell in 3'-position is linked via a linker with a reporter gene and in 5'-position is in operative linkage with an expression control sequence.

The procedure in the method according to the invention for identifying frameshift mutations moreover corresponds to the previously described method.

In one embodiment, the provision of a host cell in step (i) of the method involves the introduction of an expression vector into a host cell, wherein the expression vector comprises the double-stranded nucleic acid which comprises a coding target nucleic acid and a coding opposite strand nucleic acid complementary thereto. In the expression vector, the opposite strand nucleic acid is preferably joined with a linker in 3'-position which comprises the translational coupler sequence.

The opposite strand nucleic acid in the expression vector is preferably in operative linkage with an expression control sequence in 5'-position. In a particularly preferred embodiment, the opposite strand nucleic acid in the expression vector in 3'-position is linked via a linker with a reporter gene and in 5'-position is in operative linkage with an expression control sequence.

The expression vector and optionally reporter vector is/are introduced into the host cell in accordance with methods known in the prior art, for example by (co)transfection, (co)transformation or (co)infection of cells. The method is preferably selected such that the double-stranded nucleic acid is introduced into the host cell in such a way that, in the host cell, the opposite strand sequence is linked with the reporter gene via the linker which comprises a translational coupler sequence.

In a preferred embodiment, in step (i) of the method a vector is provided which, in addition to the reporter gene linked via a linker with the opposite strand nucleic acid, comprises at least one selection marker gene.

FIGURES

FIG. 1 shows the plasmid map of an expression vector according to the invention. Kanamycin resistance is present as the reporter gene downstream of the opposite strand nucleic acid MCS. FIG. 1 discloses the amino acid sequence as SEQ ID NO: 17 and the nucleic acid sequence as SEQ ID NO: 16.

Figure 2:
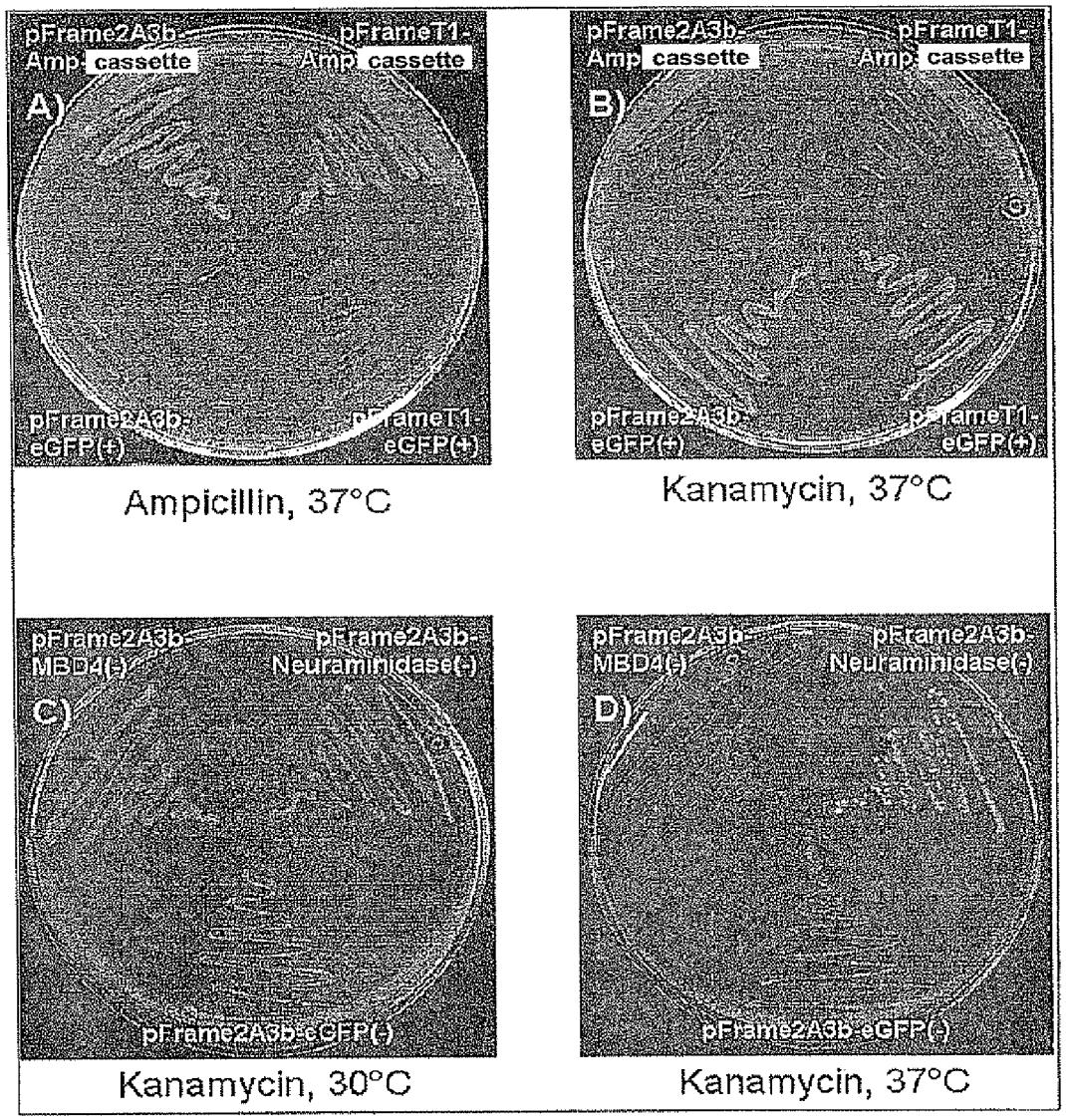

FIG. 2 Streaked plates of colonies with kanamycin selection vectors (pFrame2A3b and pFrameT1) with different KpnI/SacI insertions. The insertions on plate A) and B) comprise, on the one hand, beta-lactamase including promoter (A and B, top), which is cloned in reverse orientation to the kanamycin resistance gene and imparts amp resistance but does not permit kana resistance, since the opposite strand of promoter+beta-lactamase does not contain an open reading frame, and, on the other hand, eGFP (C and D), which is present here cloned in identical orientation and in-frame to the kanamycin resistance gene. Here, the continuous reading frame of the plus strand of eGFP enables expression of kanamycin resistance, while the absence of the ampicillin cassette naturally does not permit any growth on ampicillin. These data demonstrate that a selection for sequences with open reading frames is possible with the assistance of the method according to the invention.

In contrast, three colonies are streaked on plates C) and D), which colonies contain three different insertions in negative orientation in the pFrame2A3b kanamycin selection vector, all three also having an open reading frame in the minus strand. The insertions comprise the genes for eGFP (735 bp), influenza neuraminidase (1398 bp) and human CpG-binding protein MBD4 (1755 bp).

All three constructs are thus capable of growing on kanamycin. It is, however, also clear in individual cases, namely in particular MBD4(−) and to a lesser extent also neuraminidase (−) and eGFP(−), that growth is stabler at 30° C. instead of 37° C.

These three fusion proteins from minus strand translation plus neomycin phosphotransferase are thus capable of imparting phenotypic and selectable kanamycin resistance.

FIG. 3 shows the sequences of the three insertions from FIG. 2 with annotated plus and minus translation. FIG. 3A discloses SEQ ID NOS 2, 1, 3 and 4, respectively, in order of appearance. FIG. 3B discloses SEQ ID NOS 6, 5, 7, 18 and 8, respectively, in order of appearance. FIG. 3C discloses SEQ ID NOS 10, 9, 11 and 12, respectively, in order of appearance.

Figure 4:
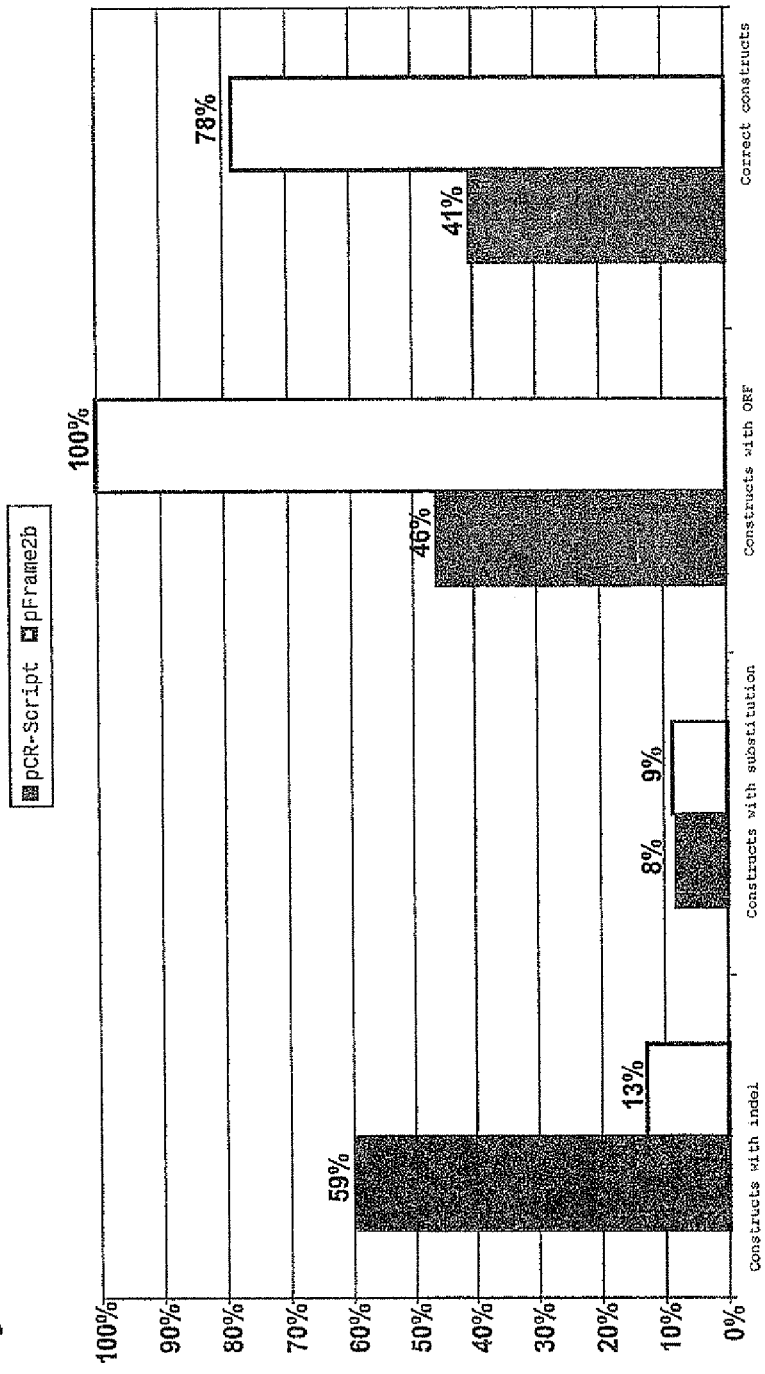

FIG. 4 illustrates a comparison of the selection of coding nucleic acid constructs for the absence of frameshift mutations with the assistance of a conventional cloning vector and a cloning vector according to the invention. The grey bars show the result of selection using the conventional pCR Script cloning vector, while the white bars show the result of selection using the pFr2b selection vector according to the invention.

FIG. 5 shows a partial sequence of a pFroup1 vector for use in the method of the invention. The opposite strand nucleic acid (insert) was linked via a linker with a kanamycin resistance gene (kan2). The linker shown in each case contains a plurality of stop codons in the reading frames shifted by +1 and by −1 relative to the reading frame of the opposite strand sequence. The linker furthermore contains a translational coupler sequence (TAA ATG), the stop codon of which is in frame to the reading frame of the opposite strand nucleic acid, and the start codon of which is in frame to the kanamycin resistance gene. FIG. 5 discloses SEQ ID NOS 14, 13, 15 and 19-21, respectively, in order of appearance.

Figure 6:
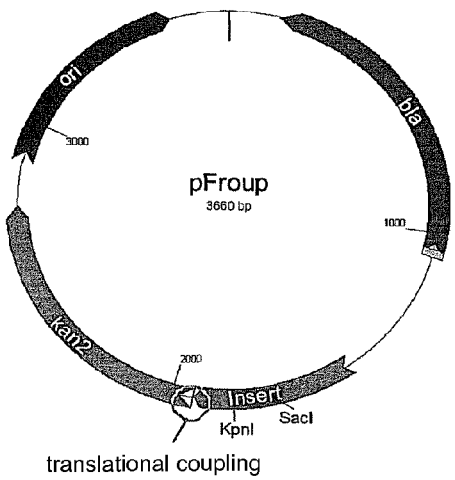

FIG. 6 shows the structure of the pFroup1 and pFroup2 vectors according to the invention. Both are designed for use in E. coli. The plasmid imparts ampicillin resistance to the host cell, independently of an insert, so ensuring straightforward multiplication. The insert to be investigated is cloned into the vector via the KpnI and SacI restriction sites. Expression is under the control of a constitutive promoter.

Figure 7:
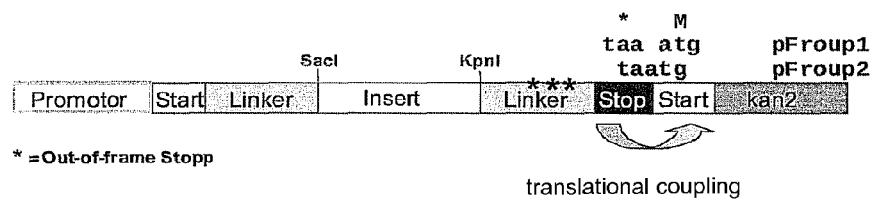

FIG. 7 shows the coupling of the insert and kan2. A linker is fused N-terminally to the insert, the linker bearing stops in the +1 and −1 reading frame (out-of-frame stops). In the case of deletions and insertions which shift the reading frame, translation is terminated at this point. Only if the insert is correctly translated is the resistance marker synthesised via translational coupling, which in this case results in kanamycin resistance of the host cell.

Figure 8:
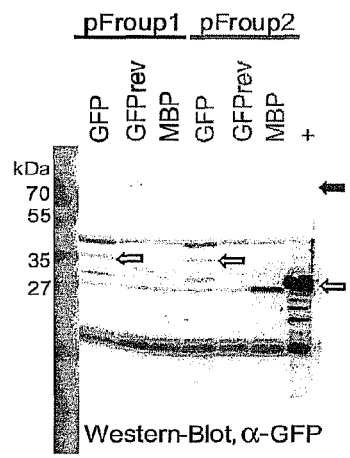

FIG. 8 shows the result of an immunoblot analysis of the expression product of a nucleic acid sequence coding for GFP which was inserted into the plasmids pFroup1 and 2. The GFP synthesised in the transformed cells was investigated by immunoblot in order to establish that translational coupling results in the formation not of a large fusion protein, but instead of two separate polypeptide chains. The controls used were cells which had been transformed with GFPrev, the opposite strand nucleic acid of GFP, which codes for a nonsense polypeptide, or MBP. Free GFP has a size of 40 kDa (white arrow), the GFP-Kan2 fusion protein would be 70 kDa in size (black arrow). GFP from a comparison vector is applied as a positive control (+). Since no linker is present N-terminally here, it is only approx. 30 kDa in size. Translational coupling is functional both in pFroup1 and in pFroup2. Accordingly, no detectable Kan2 fusion protein is formed.

The following exemplary embodiments are intended to provide further illustration of the invention.

EXAMPLE 1

Selection for Absence of Frameshift Mutations

A construct produced entirely from oligonucleotides with a length of 684 bp was cloned into the conventional pCR Script cloning vector and into the pFr2b selection vector according to the invention via the restriction enzymes KpnI/SacI. The sequence of the construct was designed by alternative codon selection such that, in addition to the biologically relevant reading frame (with a terminal stop codon), it comprises a second open reading frame in reverse direction. This does not, however, have any effect on the biologically relevant protein coded on the sense strand.

Ligation of the construct (insert) into the pFr2b vector gives rise to an open reading frame within the vector which is composed of start+reverse insert+selection gene (kana). Only if the insert's reading frame is intact can kana be correctly translated and enable growth of the cell/colony.

The ligations were transformed into E. coli and plated out onto selection plates comprising 50 μg/ml of kanamycin. Plasmid DNA was isolated from individual grown colonies, sequenced and analysed in accordance with the following criteria listed in Table 1.

TABLE 1

| | Construct Vector | |
| --- | --- | --- |
| | 0800349 pCR-Script | 0800349 pFr2b |
| Orientation | Reverse | Reverse |
| Size | 684 bp | 684 bp |
| Peer group | 37 | 23 |
| Total insertions | 12 | 0 |
| Insertions per construct | 0.32 | 0.00 |
| Insertions per kb | 0.47 | 0.00 |
| Total deletions | 20 | 4 |
| Deletions per construct | 0.54 | 0.17 |
| Deletions per kb | 0.79 | 0.25 |
| Constructs with indel | 22 | 3 |
| Constructs with indel (%) | 59% | 13% |
| Constructs with in-frame indel | 2 | 3 |
| Constructs with in-frame indel (%) | 5% | 13% |
| Total transitions | 2 | 2 |
| Transitions per construct | 0.05 | 0.09 |
| Transitions per kb | 0.08 | 0.13 |
| Total transversions | 1 | 0 |
| Transversions per construct | 0.03 | 0.00 |
| Transversions per kb | 0.04 | 0.00 |
| Constructs with substitution | 3 | 2 |
| Constructs with substitution (%) | 8% | 9% |
| Constructs with ORF | 17 | 23 |
| Constructs with ORF (%) | 46% | 100% |
| Constructs without indels | 15 | 20 |
| Constructs without indels (%) | 41% | 87% |
| Correct constructs | 15 | 18 |
| Correct constructs (%) | 41% | 78% |

| | Indels | |
| --- | --- | --- |
| | pCR script | pFr2b |
| >3 bp del (size) | 3 (8 bp, 591 bp, 456 bp) | 0 |
| 3 bp del | 0 | 2 |
| 2 bp del | 1 | 1 |
| 1 bp del | 15 | 1 |
| 1 bp ins | 12 | 0 |
| 2 bp ins | 0 | 0 |
| 3 bp ins | 0 | 0 |
| >3 bp ins | 0 | 0 |

The terms and abbreviations used in Table 1 above have the following meanings:
Construct Name of the construct. The gene was in each case cloned into the vectors via KpnI/SacI.
Vector pCR-Script: conventional cloning vector; pFr2b: selection vector according to the invention for open reading frames
Orientation Orientation in which cloning into the vector was performed. Only of relevance to pFr2b. Cloning was therefore performed here such that the reverse reading frame of the gene is present in fused form with the selection cassette.
Size Length of the gene in bp.
Peer group Number of sequenced clones.
Total insertions Total number of insertions found in the random sample.
Insertions per construct Calculated insertions per construct.
Insertions per kb Calculated insertions per kilobase.

Total deletions Total number of deletions found in the random sample.
Deletions per construct Calculated deletions per construct.
Deletions per kb Calculated deletions per kilobase.
Constructs with indel Total number of constructs found in the random sample with at least one insertion or deletion. In the case of pFr2b, this is not identical to the sum of all insertions deletions, since in this case there is one construct with two deletions, for example.
Constructs with indel (%) Percentage of constructs in the random sample with at least one insertion or deletion. Distinctly fewer constructs with indels are found in the case of pFr2b (13% vs. 59%). See FIG. 4.
Constructs with in-frame indel Total number of constructs found in the random sample with at least one insertion or deletion which, however, does not interrupt the reverse open reading frame. It should be noted that in the case of pFr2b the three constructs with an indel still nevertheless comprise an intact reverse open reading frame. The reason for this is that two constructs have a 3 bp deletion, one construct has a 1 bp deletion and shortly thereafter also a 2 bp deletion; these do not interrupt the reading frame since the deletions are divisible by three, as is mentioned in the general part of the description.
Constructs with in-frame indel (%) Percentage of constructs found in the random sample with at least one insertion or deletion which, however, does not interrupt the reverse open reading frame.
Total transitions Total number of transitions found in the random sample (purine <–> purine or pyrimidine <–> pyrimidine).
  The fact that transitions are more frequently observed than transversions indicates that the substitutions were not introduced by oligonucleotide errors, but instead by PCR errors.
Transitions per construct Calculated transitions per construct.
Transitions per kb Calculated transitions per kilobase.
Total transversions Total number of transversions found in the random sample (purine <–> pyrimidine).
Transversions per construct Calculated transversions per construct.
Transversions per kb Calculated transversions per kilobase.
Constructs with substitution Total number of transitions+transversions (=substitutions) found in the random sample.
Constructs with substitution (%) Percentage of constructs in the random sample with at least one substitution. No selection is made by pFr2b with regard to substitutions. See FIG. 4.
Constructs with ORF Total number of constructs found in the random sample with a reverse open reading frame.
Constructs with ORF (%) Percentage of constructs in the random sample with a reverse open reading frame. It should be noted that this value is 100% in the case of pFr2b. See FIG. 2.
Constructs without indels Total number of constructs found in the random sample without an insertion or deletion.
Constructs without indels (%) Percentage of constructs in the random sample without an insertion or deletion. It should be noted that this value is 87% in the case of pFr2b, i.e. more than twice as high as without corresponding selection.
Correct constructs Total number of constructs found in the random sample which have neither an insertion or deletion, nor a substitution, which are thus 100% correct.
Correct constructs (%) Percentage of constructs in the random sample which have neither an insertion or deletion, nor a substitution, which are thus 100% correct. It should be noted that this value is 87% in the case of pFr2b, i.e. almost twice as high as without corresponding selection. See FIG. 4.
>3 del (size) Total number of deletions of >3 bp found in the random sample and their size.
3 del Total number of deletions of 3 bp found in the random sample.
2 del Total number of deletions of 2 bp found in the random sample.
1 del Total number of deletions of 1 bp found in the random sample.
1 ins Total number of insertions of 1 bp found in the random sample.
2 ins Total number of insertions of 2 bp found in the random sample.
3 ins Total number of insertions of 3 bp found in the random sample.
>3 ins Total number of insertions of >3 bp found in the random sample.
Result:
  In the example given, cloning into the pFr2b selection vector leads to 100% elimination of those inserts whose reading frame has been destroyed by insertions or deletions. However, no selection occurs for the far rarer substitution mutations. Insertions/deletions which leave the reading frame intact are likewise not eliminated.
  Overall, selection in the example given led to a yield of 78% correct constructs, whereas without selection only 41% of the constructs were correct. The result of the selection investigation is shown in FIG. 2.

EXAMPLE 2

The pFroup1 and 2 vectors illustrated in FIGS. 5-7 were synthesised, in which a nucleic acid to be investigated (insert) is linked with a reporter gene via a linker which comprises a translational coupler sequence. The vectors differ with regard to the nature of the translational coupling. In pFroup1 the stop and start consist of two separate codons (TAA ATG). In pFroup2 the stop codon overlaps with the start codon (TAATG). Any desired nucleic acid to be checked for frameshift mutations may be inserted at the position of the insert.

First of all, model inserts were purposefully tested to check the functionality of the vectors according to the invention. In doing so, a nucleic acid sequence coding for the green fluorescent protein (GFP), the reverse complementary sequence thereto (GFPrev) and part of the maltose binding protein (MBP) was inserted as insert into pFroup1 and 2. The GFP and GFPrev sequences have a correct reading frame, while the MBP insert does not have a sequence divisible by three and thus does not have a correct reading frame.

Functioning of the vectors was first of all demonstrated in a growth test. E. coli host cells containing the pFroup-GFP and pFroup-GFPrev vectors exhibited resistance to ampicillin and kanamycin. The pFroup-MBP vector does not impart kanamycin resistance to the host cell, as here, due to the incorrect reading frame, the Kan2 polypeptide is not formed due to premature termination of translation in the linker zone. In order to rule out the kanamycin resistance of the pFroup-GFP construct being due to the formation of a fusion protein from GFP and Kan2 (this could occur in pFroup1 bp skipping the stop codon), the synthesised GFP was investigated by immunoblot analysis (FIG. 8). It was possible to detect the free GFP, but not a very much larger GFP-Kan2 fusion protein. Correct functioning of translational coupling in the developed pFroup1 and 2 vectors was thus demonstrated.

The invention claimed is:

1. A method for identifying frameshift mutations in coding target nucleic acids comprising one or more stop codons which comprises the steps:
  (i) providing a host cell comprising a double-stranded nucleic acid, which comprises a coding target nucleic acid and a coding opposite strand nucleic acid complementary thereto, in which the opposite strand nucleic acid is linked via a linker with a reporter gene in 3'-position; wherein the linker comprises a translational coupler sequence which comprises a stop codon in frame to the reading frame of the opposite strand nucleic acid and a start codon,
    wherein the reporter gene is in frame to the start codon
    wherein the linker comprises further stop codons in reading frames shifted by +1 and −1,
    wherein the further stop codons are located upstream of the stop codon of the translational coupler sequence,
    wherein the distance from the further stop codon to the start codon of the translational coupler sequence is at least 30 base pairs, such that no translational coupling occurs,
  (ii) effecting expression of the opposite strand nucleic acid; and
  (iii) identifying whether expression of the reporter gene occurs in the host cell, in which expression of the reporter gene indicates that the target nucleic acid does not comprise a frameshift mutation.

2. A method according to claim 1, wherein the start and stop codons of the translational coupler sequence follow on immediately from one another.

3. A method according to claim 1, wherein the start and stop codons of the translational coupler sequence overlap with one another.

4. A method according to claim 1, wherein the start and stop codons of the translational coupler sequence are at a distance from one another which is selected such that translational coupling is enabled.

5. A method according to claim 1, in which the opposite strand nucleic acid is furthermore in operative linkage with an expression control sequence in 5'-position.

6. A method according to claim 1, in which step (i) comprises: introducing an expression vector comprising the double stranded nucleic acid into a host cell.

7. A method according to claim 6, in which the opposite strand nucleic acid in the expression vector is in operative linkage with an expression control sequence in 5'-position.

8. A method according to claim 6, in which an expression vector is used in step (i) which additionally comprises at least one selection marker gene.

9. A method according to claim 8, in which the selection marker gene is constitutively expressed.

10. A method according to claim 6, in which the expression vector is introduced by calcium phosphate coprecipitation, lipofection, electroporation, particle bombardment or viral infection.

* * * * *